(12) United States Patent
Tebbs et al.

(10) Patent No.: US 9,175,354 B2
(45) Date of Patent: Nov. 3, 2015

(54) **DETECTION OF *SALMONELLA ENTERICA* SUBSPECIES *ENTERICA* SEROVAR *ENTERITIDIS* IN FOOD AND ENVIRONMENTAL SAMPLES, METHODS AND COMPOSITIONS THEREFOR**

(75) Inventors: Robert Tebbs, Livermore, CA (US); Craig Cummings, Pacifica, CA (US); Arlene Nunez, San Jose, CA (US); Priya Balachandran, Foster City, CA (US); Payman Fatemi, Pleasanton, CA (US); Olga Petrauskene, San Carlos, CA (US)

(73) Assignee: Life Technologies Corporation, Carlsbad, CA (US)

( * ) Notice: Subject to any disclaimer, the term of this patent is extended or adjusted under 35 U.S.C. 154(b) by 253 days.

(21) Appl. No.: 13/197,758

(22) Filed: Aug. 3, 2011

(65) Prior Publication Data

US 2012/0034606 A1 Feb. 9, 2012

Related U.S. Application Data

(60) Provisional application No. 61/370,393, filed on Aug. 3, 2010.

(51) Int. Cl.
*C12Q 1/68* (2006.01)
(52) U.S. Cl.
CPC .......... *C12Q 1/689* (2013.01); *C12Q 2561/113* (2013.01); *C12Q 2600/156* (2013.01)
(58) Field of Classification Search
None
See application file for complete search history.

(56) References Cited

PUBLICATIONS

GenBank Accession No. U66901.1 for *Salmonella enteritidis* fimbrial biosynthesis protein (Prot6e) gene, Sep. 5, 1996 [online], [retrieved on Feb. 24, 2013], retrieved from the Internet: <URL: http://www.ncbi.nlm.nih.gov/nuccore/u66901>.*

Real-Time PCR Systems Chemistry Guide (2005) 138 pages.*
Clavijo et al., "Identification of Genes Associated with Survival of *Salmonella enterica* Serovar *Enteritidis* in Chicken Egg Albument", *Applied and Environmental Microbiology*, vol. 72, No. 2, Feb. 2006, 1055-1064.
Day et al., "Development of a Cell Culture Method to Isolate and Enrich *Salmonella enterica* Serotype *Enteritidis* from Shell Eggs for Subsequent Detection by Real-Time PCR", American Society for Microbiology, vol. 75, No. 16, Aug. 2009, 5321-5327.
Hadjinicolaou et al., "Molecular beacon-based real-time PCR detection of primary isolates of *Salmonella typhimurium* and *Salmonella Enteritidis* in environmental and clinical samples", Department of Biological Sciences, May 19, 2009, 14.
Lee et al., "A multiplex real-time PCR for differential detection and quantification of *Salmonella* spp., *Salmonella enterica* serovar Typhimurium and *Enteritidis* in meats", Journal of Veterinary Science, vol. 10, Issue 1, 2009, 43-51.
Malorny et al., "A real-time PCR for the detection of *Salmonella enteritidis* in poultry meat and consumption eggs", Journal of Microbiological Methods, vol. 70,, 2007, 245-251.
Mozola et al., "Evaluation of the GeneQuence DNA Hybridization Method in Conjunction with 24-Hour Enrichment Protocols for Detection of *Salmonella* spp. in Select Foods: Collaborative Study", Journal of AOAC International, vol. 90, No. 3, 2007, 738-755.
Seo et al, "Rapid, Specific Detection of *Salmonella enteritidis* in Pooled Eggs by Real-Time PCR," Journal of Food Protection, vol. 67, No. 5, May 1, 2004, 864-869.
Woodward et al., "Detection of *Salmonella enteritidis* in eggs by the polymerase chain reaction", Veterinary Record, vol. 138, 1996, 411-413.

* cited by examiner

*Primary Examiner* — Angela M Bertagna
(74) *Attorney, Agent, or Firm* — Thompson Hine LLP

(57) ABSTRACT

Embodiments of the disclosure relate to compositions of isolated nucleic acid sequences, methods, workflows and kits of use thereof for detection of *Salmonella enterica*, subspecies *enterica*, serovar *Enteritidis* (*S. Enteritidis*) in a sample, particularly in a food (egg, poultry) or environmental sample (including poultry-related environmental samples). Embodiments of the disclosure may also be used to differentially detect *S. Enteritidis* without cross-reacting with *S. Paratyphi* C or other closely related *Salmonella* species. In some embodiments, methods and kits of the disclosure may comprise a TaqMan® assay. Following sample enrichment, methods of detection may be completed in approximately 3 hours.

12 Claims, 3 Drawing Sheets

US 9,175,354 B2

DETECTION OF *SALMONELLA ENTERICA* SUBSPECIES *ENTERICA* SEROVAR *ENTERITIDIS* IN FOOD AND ENVIRONMENTAL SAMPLES, METHODS AND COMPOSITIONS THEREFOR

CROSS REFERENCE TO RELATED APPLICATION

This patent application claims priority under 35 U.S.C. §119(e) to U.S. Provisional Patent Application Ser. No. 61/370,393, filed Aug. 3, 2010, the entire contents of which are incorporated herein by reference.

EFS INCORPORATION PARAGRAPH RELATING TO SEQUENCE LISTING

The instant application contains a Sequence Listing which has been submitted in ASCII format via EFS-Web and is hereby incorporated by reference in its entirety. Said ASCII copy, created on Aug. 2, 2011, is named LT00280_SequenceListing.txt and is 5,177 bytes in size.

FIELD OF DISCLOSURE

The present teachings relate to compositions, methods and kits for detection and identification of *Salmonella enterica* subspecies *enterica* serovar *Enteritidis*. More particularly, the specification describes compositions and kits comprising nucleic acid sequences specific and/or unique to *Salmonella enterica* subspecies *enterica* serovar *Enteritidis* and methods of use thereof. Methods for differentially detecting *Salmonella enterica* subspecies *enterica* serovar *Enteritidis* from other pathogens (such as non-*Salmonella* species) and from various other *Salmonella* serovars and strains (such as, but not limited to, *Salmonella Paratyphi* C and several other *Salmonella* spp.) are also described.

BACKGROUND

Salmonellosis (*Salmonella* infection) has been linked to the pathogen *Salmonella enterica* subspecies *enterica* serovar *Enteritidis* (*S. Enteritidis*). Poultry products, including eggs and poultry birds, serve as a reservoir for *S. Enteritidis* (SE). Poultry birds are often asymptomatic for *Salmonella* infection and hence the pathogen is difficult to detect. The pandemic of *S. Enteritidis* is believed to have started in the mid 1980s by interaction of the pathogen with poultry environment, especially hen house conditions, poultry birds, eggs as well as the human hosts who consume poultry products. The *S. Enteritidis* pathogen can pass to humans via contaminated poultry products through the food production chain. Several outbreaks have been reported where eggs were the source of human infection. Undercooked or raw eggs and poultry meat constitute a high risk of infection for humans. Two strains of *Salmonella*, both *S. Typhimurium* and *S. Enteritidis*, have been shown to infect chicken reproductive tracts and contaminate forming eggs but *S. Enteritidis* persists even after eggs are laid.

Starting Jul. 9, 2010, the US Food and Drug Administration (FDA) published new regulations that require commercial egg producers to test poultry houses and egg samples for the presence of *S. Enteritidis*. Since the levels are often low and sporadic, highly sensitive detection methods are required for robust and reliable detection of the pathogen.

A sensitive and specific detection method for the presence of *S. Enteritidis* is needed for the testing of humans, eggs, hens and other poultry-related samples.

SUMMARY OF DISCLOSURE

In some embodiments, the present disclosure describes isolated nucleic acid sequences and methods of use thereof for highly specific amplification and detection of *S. Enteritidis*. In some embodiments, compositions of isolated nucleic acid sequences of the disclosure, methods of the disclosure and kits of the disclosure, provide the ability to specifically and differentially detect *S. Enteritidis* from other *Salmonella* species, such as *Salmonella Paratyphi* C (*S. Paratyphi* C). In some embodiments, compositions, kits and methods of the disclosure prevent the cross-detection of *S. Paratyphi* C.

In some embodiments, a nucleic acid sequence of the disclosure may be described as a "target" sequence or a "target *S. Enteritidis* nucleic acid sequence" or a "target gene sequence" and may comprise isolated nucleic acid molecules coding for a gene called the Prot6e gene or a fragment thereof or a complement thereof that is found in one or more *S. Enteritidis* strains and generally absent in other non-Enteritidis organisms. In some embodiments, a target *S. Enteritidis* nucleic acid sequence may comprise isolated nucleic acid molecules comprising a nucleotide sequence having at least a 90% sequence identity, at least 80% sequence identity and/or at least 70% sequence identity to a "target *S. Enteritidis* nucleic acid sequence," a fragment thereof and/or a complement thereof.

In some embodiments, the disclosure describes isolated nucleic acid sequence compositions that are primers and/or probes. Primer sequences of the disclosure may be operable to bind to and amplify a "target nucleic acid sequence" (or to a fragment or a complementary sequence thereof) that is specific to *S. Enteritidis* and not specific to other *Salmonella* spp., serovars and strains or to other non-*Salmonella* spp. In some embodiments probe and/or primers of the disclosure comprise the nucleic acid sequences of SEQ ID NO: 1-SEQ ID NO: 15, and/or in nucleic acid molecules with at least 90% sequence homology to nucleic acid sequences of SEQ ID NO:1-SEQ ID NO:15, and/or in any nucleic acid molecule complementary to a sequence of SEQ ID NO:1-SEQ ID NO:15. These nucleic acid sequences are also described in Table 2 in which "FWDSEQ" represents the sequence of a forward primer, "REVSEQ" represents the sequence of a reverse primer, and "PROBESEQ" represents the sequence of a probe. Nucleic acid molecules having at least 90% homology with sequences of Table 2 are also embodiments of the invention, including 91%, 92%, 93%, 94%, 95%, 96%, 97%, 98%, and 99% homology. Nucleic acids of the disclosure are also described in the Sequence Listing incorporated by reference herein.

In some embodiments, isolated nucleic acid sequence compositions of the disclosure may further comprise one or more label, such as, but not limited to, a dye, a radioactive isotope, a chemiluminescent label, a fluorescent moiety, a bioluminescent label an enzyme, and combinations thereof, and may be referred to as a labeled derivative thereof.

In certain embodiments, a composition of the disclosure may comprises isolated nucleic acid molecules having a primer pair combination and may comprise a primer pair (a forward and a reverse primer combination) comprising nucleic acid molecules described for example in any row of in Table 2. A composition of the disclosure may further comprise a probe described in the same row of Table 2. A few example combinations of primer pairs (and probes) are described below. Other combinations, in light of this specification, are also encompassed by the present disclosure.

For example, a composition of the disclosure may comprise a primer pair having nucleic acid sequences of SEQ ID NO:1 and SEQ ID NO:3, or nucleic acid molecules with at least 90% sequence homology thereto and may include labeled derivatives thereof. In further embodiments, the composition may further include a probe having an isolated nucleic acid molecule having SEQ ID NO:2 or a nucleic acid molecule with at least 90% sequence homology thereto and may include labeled derivatives thereof.

In another example embodiment, a composition may comprise a primer pair having nucleic acid molecules having SEQ ID NO:4 and SEQ ID NO:6, or nucleic acid molecules with at least 90% sequence homology thereto and may include labeled derivatives thereof. In further embodiments, this composition may further comprise a probe having a nucleic acid sequence of SEQ ID NO:5 or a nucleic acid molecule with at least 90% sequence homology thereto and may include labeled derivatives thereof.

In yet another example embodiment, a composition may comprise a primer pair having nucleic acid molecules having SEQ ID NO:10 and SEQ ID NO:12, or nucleic acid molecules with at least 90% sequence homology thereto and may include labeled derivatives thereof. In further embodiments, this composition may further comprise a probe having a nucleic acid sequence of SEQ ID NO:11 or a nucleic acid molecule with at least 90% sequence homology thereto and may include labeled derivatives thereof.

As described compositions other primer pair and probe sequence combinations are described in rows of Table 2.

The disclosure also relates to recombinant constructs comprising primer pair and probe nucleic acid sequences unique to S. Enteritidis described in SEQ ID NO: 1-SEQ ID NO: 15 in sections above.

The present disclosure, in some embodiments, describes assays utilizing molecular methods such as sequence specific amplification and detection that offer significant improvements in speed, sensitivity and specificity over traditional microbiological methods. Embodiments relate to design and development of molecular detection assays comprising identification of target sequences that are present in S. Enteritidis and are absent in other related Salmonella species and serovars such as S. Paratyphi C. Detection of one or more of such a target sequence or a fragment thereof in a sample is indicative of the presence of an S. Enteritidis organism in that sample.

Composition and methods of the disclosure allow highly specific amplification and detection of S. Enteritidis and ability to distinguish S. Enteritidis from other Salmonella species, particularly S. Paratyphi C.

Some embodiments described herein provide highly specific real-time PCR assays that provide for detection of a Prot6e gene in S. Enteritidis or complements and/or fragments thereof that is conserved in S. Enteritidis. Some methods of the disclosure are operable to detect S. Enteritidis genomic DNA. In some embodiments, methods of the disclosure are able to detect S. Enteritidis with no cross-reactivity with S. Paratyphi C.

In some embodiments, a method for determining the presence of S. Enteritidis in a sample may comprise combining the sample with a culture medium for enriching Salmonella species (if present in the sample) for a time to generate a enriched sample of Salmonella; extracting nucleic acid from at least some of the enriched sample to obtain extracted nucleic acid; contacting the extracted nucleic acid with at least one primer pair under conditions to generate an amplified nucleic acid, wherein the primer pair is designed to bind to and amplify a target gene or fragment thereof that is specific to S. Enteritidis; and detecting at least some of the amplified nucleic acid, thereby determining the presence of S. Enteritidis in the sample. Absence of any amplified nucleic acid is indicative of the absence of S. Enteritidis in the sample.

Detection according to some embodiments of the disclosure may comprise contacting the amplified nucleic acid with a probe; and detecting the hybridization of probe with the amplified nucleic acid. Detection may be performed by a variety of methods, such as but not limited to, by a nucleic acid amplification reaction. In some embodiments the amplification reaction maybe an end-point determination or the amplification reaction maybe quantitative. The quantification may be a real-time PCR method. In some embodiments, the real-time PCR may be a SYBR® Green Assay or a TaqMan® Assay. Detection, in some embodiments, maybe performed by hybridization using probes specific to target sequences. According to some embodiments, combinations of amplification and hybridization may be used for detection.

Exemplary amplification methods include polymerase chain reaction (PCR; see, e.g., U.S. Pat. Nos. 4,683,202; 4,683,195; 4,965,188; and 5,035,996), isothermal procedures (using one or more RNA polymerases (see, e.g., WO 2006/081222), strand displacement (see, e.g., U.S. Pat. No. RE39007E), partial destruction of primer molecules (see, e.g., WO2006087574)), ligase chain reaction (LCR) (see, e.g., Wu, et al., Genomics 4: 560-569 (1990) and/or Barany, et al. PNAS USA 88:189-193 (1991)), Qβ RNA replicase systems (see, e.g., WO/1994/016108), RNA transcription-based systems (e.g., TAS, 3SR), rolling circle amplification (RCA) (see, e.g., U.S. Pat. No. 5,854,033; U.S. Pub. No. 2004/265897; Lizardi et al., Nat. Genet. 19: 225-232 (1998); and/or Bailer et al. Nucleic Acid Res., 26: 5073-5078 (1998)), and strand displacement amplification (SDA) (Little, et al. Clin Chem 45:777-784 (1999)), among others. Many systems are suitable for use in amplifying target nucleic acids and are contemplated herein as would be understood by one of skill in the art.

Any of several methods may be used to detect amplified target nucleic acids using primers and/or probes. Many different reagents, systems, and/or detectable labels may be used in the methods described herein. These include, for example, TaqMan® systems, detectable label-quencher systems (e.g., FRET, salicylate/DTPA ligand systems (see, e.g., Oser et al. Angew. Chem. Int. Engl. 29(10):1167 (1990), displacement hybridization, homologous probes, assays described in EP 070685), molecular beacons (e.g., NASBA), Scorpion, locked nucleic acid (LNA) bases (Singh, et al. Chem Commum 4:455-456 (1998)), peptide nucleic acid (PNA) probes (Pellestor, et al. European J. Human Gen. 12:694-700 (2004)), Eclipse probes (Afonina, et al. Biotechniques 32:940-949 (2002)), light-up probes (Svanvik, et al. Anal Biochem 281:26-35 (2001)), molecular beacons (Tyagi, et al. Nat. Biotechnol. 14:303-308 (1996)), tripartite molecular beacons (Nutiu, et al. Nucleic Acids Res. 30:e94 (2002)), QuantiProbes, HyBeacons (French, et al. Mol. Cell. Probes 15:363-374 (2001)), displacement probes (Li, et al. Nucliec Acids Res. 30:e5 (2002)), HybProbes (Cardullo, et al. PNAS 85:8790-8794 (1988)), MGB Alert, Q-PNA (Fiandaca, et al. Genome Res. 11:609-611 (2001)), Plexor, LUX primers (Nazarenko, et al. Nucleic Acids Res. 30:e37 (2002)), Scorpion primers (Whitcombe, et al. Nat Biotechnol 17:804-807 (1999)), AmpliFluor (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products may be monitored while the reaction is in progress. An apparatus for detecting the signal generated by the detectable label may be used to detect, measure, and quantify the signal before, during, and/or after amplification. The particular type of signal may dictate the choice of detection method. For example, in some embodiments, fluorescent dyes are used to label probes and/or amplified products. The probes bind to single-stranded and/or double-stranded amplified products, and/or the dyes intercalate into the double-stranded amplified products, and consequently, the resulting fluorescence increases as the amount of amplified product increases. In some embodiments, the $T_m$ is ascertained by observing a fluorescence decrease as the double-stranded amplified product dissociates and the intercalating dye is released therefrom. The amount of fluorescence may be quantitated using standard equipment such as a spectra-fluorometer, for example. The use of other methods and/or reagents is also contemplated herein as would be understood by one of skill in the art in view of the teachings of this specification.

In some embodiments, a method of the disclosure may comprise contacting the extracted nucleic acid with at least one primer pair selected from a first primer pair having SEQ ID NO:1 and SEQ ID NO:3, and/or a second primer pair having SEQ ID NO:4 and SEQ ID NO:6, and/or a third primer pair having SEQ ID NO:7 and SEQ ID NO:9, and/or a fourth primer pair having SEQ ID NO:10 and SEQ ID NO:12, and/or a fifth primer pair having SEQ ID NO:13 and SEQ ID NO:15, and/or a primer pair having nucleic acid molecules with at least 90% sequence homology to the primer pair sequences, under conditions to generate amplified nucleic acid; and detecting at least some of the amplified nucleic acid, thereby determining the presence of S. Enteritidis species in the sample.

In embodiments comprising contacting an extracted nucleic acid molecule with at least one primer pair having at least 90% sequence homology to the primer pair sequences described above, the primer pairs may have 91%, 92%, 93%, 94%, 95%, 96%, 97%, 98%, and 99% homology to the primer pair sequences.

In some embodiments, at least two or more of the primer pairs described above may be used in a multiplex detection method. This may increase specificity of detection.

In some embodiments, an amplification product generated using the first primer pair maybe detected using a first probe having SEQ ID NO:2, an amplification product generated using the second primer pair maybe detected using a second probe having SEQ ID NO:5, an amplification product generated using the third primer pair maybe detected using a third probe having SEQ ID NO:8, an amplification product generated using the fourth primer pair maybe detected using a fourth probe having SEQ ID NO:11, and an amplification product generated using the fifth primer pair maybe detected using a fifth probe having SEQ ID NO:14. Further, detection may in some embodiments comprise contacting an amplified product using a probe having a nucleic acid molecule having at least 90% sequence homology to SEQ ID NO:2, SEQ ID NO:5, SEQ ID NO:8, SEQ ID NO:11, or SEQ ID NO:14. Accordingly, probe sequences may have 91%, 92%, 93%, 94%, 95%, 96%, 97%, 98%, and 99% homology to the corresponding probe sequences. In some embodiments, a probe may be a TaqMan® probe.

In some embodiments, a method of the disclosure may comprise contacting an extracted nucleic acid with at least one primer pair selected from a first primer pair having SEQ ID NO:1 and SEQ ID NO:3, and/or a second primer pair having SEQ ID NO:10 and SEQ ID NO:12, and/or a third primer pair having SEQ ID NO:13 and SEQ ID NO:15, and/or a primer pair having nucleic acid molecules with at least 90% sequence homology to the primer pair sequences, under conditions to generate amplified nucleic acid; and detecting at least some of the amplified nucleic acid, thereby determining the presence of S. Enteritidis species in the sample Detecting at least some of the amplified nucleic acid is indicative of the presence of S. Enteritidis in the sample. In some embodiments, the method does not detect S. Paratyphi C if it is present. In some embodiments, at least two or more of the primer pairs described above may be used in a multiplex detection method. In some embodiments, an amplification product generated using the first primer pair maybe detected using a first probe having SEQ ID NO:2, amplification product generated using the second primer pair maybe detected using a second probe having SEQ ID NO:11, and amplification product generated using the third primer pair maybe detected using a third probe having SEQ ID NO:14. Further, detection may in some embodiments comprise contacting an amplified product using a probe having a nucleic acid molecule having at least 90% sequence homology to SEQ ID NO:2, SEQ ID NO:11, or SEQ ID NO:14. Accordingly, probe sequences may have 91%, 92%, 93%, 94%, 95%, 96%, 97%, 98%, and 99% homology to the corresponding probe sequences. In some embodiments, a probe may be a TaqMan® probe.

A S. Enteritidis-specific assay, as used herein, refers to a primer/probe set that is designed to amplify a portion of the Prot6e gene of S. Enteritidis without amplifying and/or detecting S. Paratyphi C or other Salmonella species.

The S. Enteritidis-specific assay was evaluated for detection of S. Enteritidis from eggs and environmental samples as provided in Example 3 herein. Robust detection of S. Enteritidis was observed without cross-reacting with S. Paratyphi C.

Detection using the real-time PCR assay reduced the time-to-result to less than 27 hours, while allowing for sensitive detection from the complex food and environmental samples. The streamlined workflow offers a great advantage over existing culture confirmation methods by reducing the time-to-result to under 3 h following pre-enrichment. Traditional culture confirmation can take 9 to 10 days for egg samples and 4 to 5 days for environmental samples.

The robustness of the assay allows for addition of more sample volume. Therefore, further embodiments include the step of pooling samples to be tested prior to using the duplexed assay described herein The disclosure also describes several kit embodiments for detecting S. Enteritidis and may comprise at least one primer pair having hybridization specificity for amplifying a Prot6e gene or fragment thereof that is present in S. Enteritidis and not other Salmonella species.

In some embodiments, a kit of the disclosure may be created by lyophilizing reagents for a real-time PCR assay (such as primer sequences and optionally probe sequences) together with reagents of a PCR master mix. Kits having these features provide a convenient format since use of such a kit merely requires the addition of sample to the lyophilized kit reagent. Kits may sometimes also comprise sample preparation reagents such as DNA extraction reagents.

Exemplary kits of the disclosure may comprise at least one primer pairs of isolated nucleic acid molecules of SEQ ID NO:1 and SEQ ID NO:3, or SEQ ID NO:10 and SEQ ID NO:12, or SEQ ID NO:13 and SEQ ID NO:15, or a nucleic acid molecule with at least 90% sequence homology to said primer pair sequences, including 91%, 92%, 93%, 94%, 95%, 96%, 97%, 98%, and 99% homology. Other kits are also described.

These and other features of the present teachings will become more apparent from the description herein.

BRIEF DESCRIPTION OF DRAWINGS

The skilled artisan will understand that the drawings, described below, are for illustration purposes only. The drawings are not intended to limit the scope of the present teachings in any way.

DETAILED DESCRIPTION OF VARIOUS EMBODIMENTS

Figure 1:
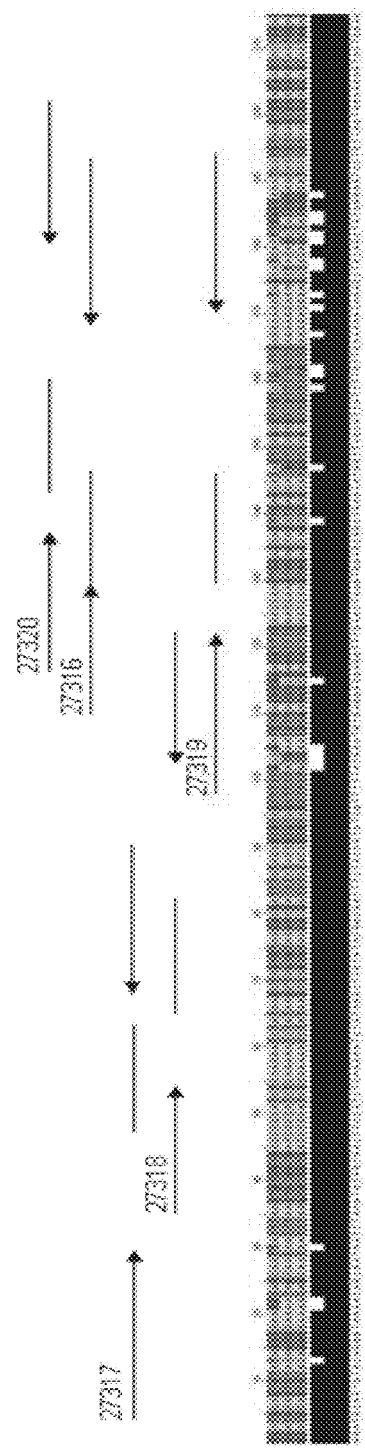
FIG. 1 provides an alignment of oligonucleotides to the Prot6e target region. The top line is serovar Paratyphi C, the bottom two lines are S. Enteritidis. Black bars at the bottom indicate conservation.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, and treatises, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Various embodiments of this disclosure describe compositions, methods and kits for detection of S. Enteritidis organisms in samples. Some embodiments relate to differential detection of S. Enteritidis from related species.

The present disclosure in some embodiments describes designing probes and primers for identification and detection of S. Enteritidis specific target genes and fragments thereof. Some exemplary primer and probe sequences were designed using a rigorous bioinformatics assay design pipeline and are described in Table 2 as SEQ ID NO: 1-SEQ ID NO: 15. For example, Table 2 describes several primer pairs, comprising at least a first primer referred to as a forward primer and a second primer referred to as a reverse primer. In a row of Table 1, each primer pair also has a corresponding probe sequence. The terms "FORSEQ" represents the sequence of a forward primer, "REVSEQ" represents the sequence of a reverse primer, and "PROBESEQ" represents the sequence of a probe (such as for example a TAQMAN® probe).

S. Enteritidis harbors in its genome a unique 60-kb virulence plasmid with a high prevalence. The plasmid comprises a gene, called Prot6e gene encoding a surface fimbriae specific to S. Enteritidis. The role of Prot6e is not clear but it is believed that it alters the interaction of S. Enteritidis with egg albumen components. The present disclosure describes identification of regions of Prot6e gene that are unique to S. Enteritidis and that are absent in closely related species such as S. Paratyphi C which are referred to herein as "target gene" or "target nucleic acid. The disclosure also describes designing of probe and primer sequences to this region and fragments thereof of.

Compositions of the disclosure comprise primer pairs (and in some embodiments, corresponding probes) that may be used in assays for specific and efficient detection of S. Enteritidis organisms in samples.

Some compositions of the disclosure may comprise a duplexed or multiplexed set of primer pairs and probes for detection of S. Enteritidis species in a single assay. For example, a composition may comprise, at least two sets of primer pairs, a first primer set comprising a first primer (a first forward primer) and a second primer (a first reverse primer) and a second primer set comprising a first primer (a second forward primer) and a second primer (a second reverse primer), each primer set operable to amplify a different target gene or target nucleic acid fragment. The composition may also have a corresponding probe sequence that can hybridize to amplified target nucleic acids of each primer set (a first probe and a second probe). A duplexed primer set may be operable to amplify at least two different target nucleic acid sequences and their corresponding probes are operable to identify at least two different target nucleic acid sequences. Compositions of the disclosure may comprise additional primer pairs (such as three primer pairs, four primer pairs and optionally the same number of corresponding probes as well).

Some embodiments herein provide a composition comprising at least one isolated nucleic acid molecule having: a) SEQ ID NO:1-SEQ ID NO:15, b) a nucleic acid molecule with at least 90% sequence homology to SEQ ID NO:1-SEQ ID NO:15, or c) a nucleic acid molecule complementary to at least one sequence of a) or b). Further embodiments include at least one isolated nucleic acid molecule having a nucleic acid molecule with at least 90% sequence homology to SEQ ID NO:1-SEQ ID NO:15, or a nucleic acid molecule complementary to at least one sequence of a) or b), including 91%, 92%, 93%, 94%, 95%, 96%, 97%, 98%, and 99% homology.

In certain embodiments, a composition may comprise isolated nucleic acid molecules having SEQ ID NO:1 and SEQ ID NO:3, or nucleic acid molecules with at least 90% sequence homology thereto including 91%, 92%, 93%, 94%, 95%, 96%, 97%, 98%, and 99% homology. In further embodiments, this composition may further include an isolated nucleic acid molecule having SEQ ID NO:2 or a nucleic acid molecule with at least 90% sequence homology thereto, including 91%, 92%, 93%, 94%, 95%, 96%, 97%, 98%, and 99% homology.

In some embodiments, a composition may comprise isolated nucleic acid molecules having SEQ ID NO:10 and SEQ ID NO:12, or nucleic acid molecules with at least 90% sequence homology thereto. In further embodiments, this composition may further comprise an isolated nucleic acid molecule having SEQ ID NO:11 or a nucleic acid molecule with at least 90% sequence homology thereto, including 91%, 92%, 93%, 94%, 95%, 96%, 97%, 98%, and 99% homology.

In some embodiments, a composition may comprise isolated nucleic acid molecules having SEQ ID NO:13 and SEQ ID NO:15, or nucleic acid molecules with at least 90% sequence homology thereto. In further embodiments, this composition may further comprise an isolated nucleic acid molecule having SEQ ID NO:14 or a nucleic acid molecule with at least 90% sequence homology thereto, including 91%, 92%, 93%, 94%, 95%, 96%, 97%, 98%, and 99% homology.

Additional compositions are described in each row of Table 2.

In some embodiments, the disclosure describes methods of detecting in a sample the presence of *S. Enteritidis* and/or methods for detecting and differentially identifying the presence of *S. Enteritidis* over closely related strains and/or serotypes. In some embodiments, the disclosure provides methods that do not detect *S. Paratyphi* C which commonly cross reacts with *S. Enteritidis*.

In some embodiments, a method of the disclosure, may comprise detecting, in a sample, at least one (or more) nucleic acid sequence(s) having at least 10 to at least 25 nucleic acids of a target gene sequence of the Prot6e gene of *S. Enteritidis* and/or complementary sequences thereof, wherein detection of at least one nucleic acid sequence indicates the presence of an *S. Enteritidis* organism in the sample. In some embodiments this method may comprise detecting a *S. Enteritidis* organism and not detecting a *S. Paratyphi* C organism.

Methods of detection may further comprise steps of sample preparation and may also comprise identification steps (to identify a species/strain). Such embodiments are described in detail in sections below.

In some embodiments, a method of the disclosure may further comprise preparing a sample for PCR amplification (prior to hybridizing with a primer pair), for example, but not limited to (1) bacterial enrichment, (2) separation of bacterial cells from the sample, (3) cell lysis, and (4) nucleic acid extraction (e.g. total DNA, genomic DNA).

Samples may include without limitation, clinical samples, food/beverage samples, water samples, and environmental sample. Food sample may comprise raw produce, meats as well as a selectively enriched food matrix.

In some embodiments, a method for the detection of a *S. Enteritidis* in a sample comprising a) hybridizing a first pair of PCR primers comprising a forward primer and a reverse primer (e.g., selected for example from a row in Table 2 described in the Examples section) that are operable to bind to and amplify a Prot6e gene or fragment thereof found only in *S. Enteritidis* and not in other organisms; b) amplifying the Prot6e gene or fragment thereof found only in *S. Enteritidis* and not in other organisms to form an amplified target nucleic acid product; and d) detecting the amplified target polynucleotide sequence product; wherein the detection of the amplified target polynucleotide sequence product is indicative of the presence of *S. Enteritidis* in the sample.

Methods of the disclosure may include assays such as polymerase chain reactions, wherein hybridizing and amplifying of said first pair of polynucleotide primers occurs in a first vessel and said hybridizing and amplifying of said second pair of polynucleotide primers occurs in a second vessel, or hybridizing and amplifying of said first pair of polynucleotide primers and said hybridizing and amplifying of said second pair of polynucleotide primers occurs in a single vessel. The detection may be a real-time assay and the real-time assay may be a SYBR® Green dye assay or a TaqMan® assay.

Detection may be performed by a variety of methods, such as but not limited to, by a nucleic acid amplification reaction. The amplification reaction may be an end-point determination, the amplification reaction maybe quantitative, the quantification maybe a real-time PCR, the real-time PCR maybe a SYBR® Green Assay, and/or the real-time PCR may be a TaqMan® Assay. Detection in some embodiments may be performed by hybridization using probes specific to target sequences. Combinations of amplification and hybridization may be used for detection according to some embodiments.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature. For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning A Laboratory Manual, Cold Spring Harbor Laboratory Press, Cold Spring Harbor, N.Y.* The temperature for hybridization is about 5-10° C. less than the melting temperature (Tm) of the hybrid.

Methods of the disclosure, in various embodiments, may comprise providing a first probe and a second probe the probes, wherein the first and second probes are different from each other, the first probe operable to identify the first amplified target polynucleotide sequence and the second probe operable to identify the second amplified target nucleotide sequence, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye; and hybridizing the first and second probes to the PCR amplified fragments to detect the presence of the first amplified target polynucleotide sequence and the second amplified target polynucleotide sequence from the sample.

In one embodiments, a method for determining the presence of a *S. Enteritidis* in a sample comprises combining the sample with a culture medium for enriching *Salmonella* spp. for a time to generate a sample enriched for said species; extracting nucleic acid from at least some of the enriched sample; contacting the extracted nucleic acid with at least one primer pair having hybridization specificity for amplifying a Prot6e gene of *S. Enteritidis* species, or a fragment of the Prot6e gene of *S. Enteritidis* species comprising at least one primer pair selected from a first primer pair having SEQ ID NO:1 and SEQ ID NO:3, or a second primer pair having SEQ ID NO:4 and SEQ ID NO:6, or a third primer pair having SEQ ID NO:7 and SEQ ID NO:9, or a fourth primer pair having SEQ ID NO:10 and SEQ ID NO:12, or a fifth primer pair having SEQ ID NO:13 and SEQ ID NO:15, or a primer pair having nucleic acid molecules with at least 90% sequence homology to the primer pair sequences, under conditions to generate amplified nucleic acid; and detecting at least some of the amplified nucleic acid, thereby determining the presence of *S. Enteritidis* in the sample. In some embodiments, at least two of the above referenced primer pairs may be used. In some embodiments, a primer pair may be a labeled derivative.

In some embodiments, a method may comprise determining the presence of *S. Enteritidis* and not *S. Paratyphi* C in a sample. An example of such a method may comprise combining the sample with a culture medium for enriching *Salmonella* species for a time to generate a sample enriched for said species; extracting nucleic acid from at least some of the enriched sample; contacting the extracted nucleic acid with at least one primer pair, having a forward and a reverse primer, selected from a first primer pair having SEQ ID NO:1 and SEQ ID NO:3, or a second primer pair having SEQ ID NO:10 and SEQ ID NO:12, or a third primer pair having SEQ ID NO:13 and SEQ ID NO:15, or a primer pair having nucleic acid molecules with at least 90% sequence homology to the primer pair sequences, under conditions to generate amplified nucleic acid; and detecting at least some of the amplified nucleic acid, wherein detection of amplified product is indicative of the presence of *S. Enteritidis* and the absence of *S. Paratyphi* C in the sample. In some embodiments of this method, the detecting at least some of the amplified nucleic acid may comprise contacting the amplified nucleic acid with a probe such as described in Table 2 corresponding to a selected primer pair, e.g., a probe having SEQ ID NO: 2 may be used for detecting an amplified product amplified by a primer pair having SEQ ID NO:1 and SEQ ID NO:3; a probe having SEQ ID NO: 11 may be used for detecting an amplified product amplified by a primer pair having SEQ ID NO:10 and SEQ ID NO:12; a probe having SEQ ID NO: 14 may be used for detecting an amplified product amplified by a primer pair having SEQ ID NO:13 and SEQ ID NO:15. In some embodiments the probe may be a TaqMan® probe.

Several compositions of the disclosure comprising primer pair and probe sets have been assayed for specificity and efficiency in detection of *S. Enteritidis*. *S. Enteritidis* detection methods described here have been tested in a wide variety samples. *S. Enteritidis* are known to be present in food samples, in samples from the environment, or from animal or humans who are potential carriers. In particular *S. Enteritidis* is known to be present in an egg and poultry derived food and in poultry-related environmental samples. A sample for detection of *S. Enteritidis* may be an uncooked food sample such as uncooked poultry meats, eggs, and other food samples such as but not limited to foods made from eggs, vegetables, unpasteurized milk, foods made from unpasteurized milk, or dairy products, or cooked or processed foods such as hot dogs, deli meats, cheeses, poultry, ice cream, smoked fish, or seafood, for example; an environmental sample for detection of *S. Enteritidis* species may be soil, water or swabs from poultry related environment, swabs from food processing equipment processing poultry products, and other environmental samples such as but not limited to stream water, sewage, plants, or any surface that is involved with food processing.

Some embodiments herein provide real-time PCR assays for detection of *S. Enteritidis* without cross-reacting with *S. Paratyphi* C (*S. Enteritidis*-specific assays). FIG. 1 shows the alignment of the Prot6e target regions of *S. Enteritidis* and *S. Paratyphi* C. Table 8 gives the map positions on GenBank Accession No. AB041905.1 of the primers and probes developed and used herein. Table 2 gives the sequences of the primer and probes. In some embodiments, the PCR assays are end-point assays.

Samples and Sample Preparation

*S. Enteritidis* for detection using methods provided herein may be present in eggs, in samples from the environment, or from animal or humans who are potential carriers (particularly in hen houses). A sample for detection of *S. Enteritidis* may be uncooked poultry, eggs and/or egg shells; an environmental sample for detection of *S. Enteritidis* may be any sample from, for example a hen-house or a turkey house, egg shells, soil, stream water, sewage, plants, swabs from chick box paper or swabs from food processing equipment, or any surface that is involved with food processing. Further, swabs from matrices with high levels of PCR inhibitory substances such as meconium can be used. Other samples include other animals that may be reservoirs for *S. Enteritidis*, other foods that may harbor *S. Enteritidis* and biological samples from human (or animals) that may harbor and/or be infected by *S. Enteritidis*.

Typically a portion of egg or a swabbed sample is combined with an appropriate liquid, such as water, a buffer solution, or a culture medium such as a selective medium or an enrichment medium. In some embodiments, a sample is chopped, macerated, liquefied, diced, or homogenized. In some embodiments, large volumes of sample, for example but not limited to, volumes of 100 mL, 250 mL, or more are processed or a portion of a sample are typically combined to form a dilute suspension, for example but not limited to, ratios of about 1:5, 1:10, or 1:20 (w/vol). In certain embodiments, 25 grams of a solid sample may be combined with 225 mL of a suitable culture media. In some embodiments, 25 mL of a liquid is combined with 225 mL of a suitable culture media.

Samples may also be pooled to save on testing costs, e.g., instead of testing 15×25 g samples of sample, a composite of 375 g, with 25 g coming from different lots of sample are tested. If any composite is tested positive, then the individual 15 samples are further evaluated. If the composite is negative, then the food testing lab has saved the cost of 15 individual tests.

For egg testing, enrichment conditions may be used. For example, while testing eggs, a pool of 20 eggs (including their liquid content, i.e., the egg yolk and egg whites) can be combined to create a mixture of approximately 1000 mL. One hundred milliliters of a 10× concentrate of a culture media (10×TSB) can combined with the egg pool (i.e. 100 mL of 10×TSB is added to ~1000 mL of eggs).

Solid samples (e.g., 25 g), liquid samples (e.g., 10 mL-100 mL) or swabbed samples (resuspended in suitable liquids such as culture medium, buffers, etc., e.g., 10 mL-100 mL) can be pre-enriched for *Salmonella* species for ~2 to 4 h and up to 12-48 hours in buffered peptone water (BPW), or an equivalent thereof. After incubation, the samples are treated for nucleic acid extraction. Alternative enrichment media include Tryptic Soy Broth, Lactose Broth, Tetrathionate Broth or Brain Heart Infusion Broth, for which ingredients can be found in, for example, "Compendium of Methods for the Microbiological Examination of Foods," 4th Edition (2001) Downes and Ito, eds. American Public Health Association, or U.S. Food and Drug Administration Bacteriological Analytical Manual (BAM), Media Index on the FDA web site. Incubation for selective enrichment can be continued for 24-48 hours enrichment.

The entire volume of the enriched culture, or a portion thereof, may be concentrated and processed for detection of S. Enteritidis, for example, a one mL aliquot may be taken from 250 mL of enriched culture. The medium may be clarified by filtration prior to or after concentrating. Harvested samples can be lysed using, for example, the PrepSEQ™ Nucleic Acid Extraction Kit (Applied Biosystems) or the PrepSEQ™ RapidSpin Kit (Applied Biosystems) or any other effective lysis system that preserves nucleic acid integrity. The lysate can be amplified directly or the nucleic acid can be extracted and amplified using the S. Enteritidis-specific PCR primers provided herein. Amplification products can be detected, directly or indirectly, and the presence or absence of S. Enteritidis in the sample can be determined.

High quality DNA can be prepared by manual low throughput methods or by automated high throughput methods, depending on the number of samples being tested. An integrated workflow for automated high-throughput sample preparation may include enrichment for S. Enteritidis, lysis, binding of nucleic acids to magnetic particles, magnetic separation, followed by optional washes and elution of DNA in a PCR compatible solution. An integrated workflow for manual low-throughput sample preparation may include enrichment for S. Enteritidis, centrifugation to clarify and pellet bacteria, resuspension of bacteria in lysis buffer, followed by amplification using S. Enteritidis-specific PCR as provided herein. The integrated system may also include lyophilized reagents for the assay and data analyses software.

PCR includes introducing a molar excess of two or more extendable oligonucleotide primers to a reaction mixture comprising the test S. Enteritidis nucleic acid sample where the primers hybridize to opposite strands of DNA. The reaction mixture is subjected to a program of thermal cycling in the presence of a DNA polymerase, resulting in the amplification of the DNA sequence flanked by the primers. PCR can be real-time or end-point.

The sequence-specific portions of the primers are of sufficient length to permit specific annealing to complementary sequences, as appropriate. A primer does not need to have 100% complementarity with its target sequence for primer extension to occur. Further, a primer can be detectably labeled such that the label is detected by, for example, biochemical, chemical, immunochemical, spectroscopic, photochemical, or other detection means. A primer pair includes a "forward primer" and a "reverse primer," indicating that they are initiating nucleic acid polymerization in opposing directions from different strands of a duplex template.

As an example of primer selection, primers can be selected by the use of any of various software programs available and known in the art for developing amplification and/or multiplex systems. Exemplary programs include, PRIMER EXPRESS® software (Applied Biosystems, Foster City, Calif.) and Primer3 software (Rozen S et al. (2000), "Primer3 on the WWW for general users and for biologist programmers," Krawetz S et al. (eds) Bioinformatics Methods and Protocols: Methods in Molecular Biology. Humana Press, Totowa, N.J., pp 365-386). In the example of the use of software programs, sequence information from SEQ ID NO:1, for example, can be imported into the software. The software then uses various algorithms to select primers that best meet the user's specifications.

Primer and probe sequences having at least 90% homology to those of SEQ ID NO: 1-SEQ ID NO:15 are embodiments herein, including 91%, 92%, 93%, 94%, 95%, 96%, 97%, 98%, and 99% homology. In some embodiments, primer and probe sequences having at least 90% homology to those of SEQ ID NO: 1-SEQ ID NO:3 and SEQ ID NO: 10-SEQ ID NO:15 are embodiments herein. "Homology," as known by one of ordinary skill in the art, is the degree of sequence relatedness between nucleotide sequences as determined by matching the order and identity of nucleotides between the sequences. In one embodiment, the primer or probe sequences provided herein have 100% homology, at least 98% homology, at least 95% homology, at least 92% homology or at least 90% homology to SEQ ID NO:1-SEQ ID NO:15. Computer methods for determining homology are designed to identify the greatest degree of matching of nucleotide sequences, for example, BLASTN (Altschul, S. F., et al. (1990) J. Mol. Biol. 215:403-410).

In certain embodiments, single-stranded amplification products can be generated by methods including, without limitation, asymmetric PCR, asymmetric reamplification, nuclease digestion, and chemical denaturation. For example, single-stranded sequences can be generated by combining at least one first primer or at least one second primer from a primer set, but not both, in an amplification reaction mixture.

In some embodiments, the methods involve the use of real-time PCR. In some embodiments, a positive result involves a detectable amount of PCR product being produced before the 40 cycle. In some embodiments, the PCR is quantitative. In some embodiments, the PCR is end-point PCR and a positive result involves a detectable amount of PCR being produced at the end of the cycling.

Polymerases

The term "polymerase," as used herein, refers to a polypeptide that is able to catalyze the addition of nucleotides or analogs thereof to a nucleic acid in a template dependent manner, for example, the addition of deoxyribonucleotides to the 3' end of a primer that is annealed to a nucleic acid template during a primer extension reaction. Nucleic acid polymerases can be thermostable or thermally degradable. Suitable thermostable polymerases include, but are not limited to, polymerases isolated from Thermus aquaticus, Thermus thermophilus, Pyrococcus woesei, Pyrococcus furiosus, Thermococcus litoralis, and Thermotoga maritima. Suitable thermodegradable polymersases include, but are not limited to, E. coli DNA polymerase I, the Klenow fragment of E. coli DNA polymerase I, T4 DNA polymerase, T5 DNA polymerase, T7 DNA polymerase, and others. Examples of other polymerizing enzymes that can be used in the methods described herein include but are not limited to T7, T3, SP6 RNA polymerases; and AMV, M-MLV and HIV reverse transcriptases.

Commercially available polymerases include, but are not limited to, TAQ DNA polymerase (Invitrogen), PLATINUM®TAQ DNA polymerase (Invitrogen), SUPERTAQ® polymerase and SUPERTAQ® Plus polymerase, TAQFS® polymerase, AMPLITAQ® CS polymerase (Perkin-Elmer), AMPLITAQ® FS polymerase (Perkin-Elmer), KENTAQ1® polymerase (AB Peptide, St. Louis, Mo.), TAQUENASE® polymerase (Scien Tech Corp., St. Louis, Mo.), THERMOSEQUENASE® polymerase (Amersham), Bst polymerase, READER™ Taq DNA polymerase, VENT® DNA polymerase, $VENT_R$® DNA Polymerase, $VENT_R$® (exo⁻) polymerase and DEEPVENT® DNA polymerase, (all VENT® polymerases can be obtained from New England Biolabs), PFUTurbo™ DNA polymerase (Stratagene), Pwo polymerase, Tth DNA polymerase, KlenTaq-1 polymerase, SEQUENASE™ 1.0 DNA polymerase (Amersham Biosciences), SEQUENASE™ 2.0 DNA polymerase (United States Biochemicals), and an enzymatically active mutant and variant thereof.

Descriptions of DNA polymerases can be found in, among other places, Lehninger *Principles of Biochemistry*, 3d ed., Nelson and Cox, Worth Publishing, New York, N.Y., 2000, particularly Chapters 26 and 29; Twyman, *Advanced Molecular Biology: A Concise Reference*, Bios Scientific Publishers, New York, N.Y., 1999; Ausubel et al., *Current Protocols in Molecular Biology*, John Wiley & Sons, Inc., including supplements through May 2005; Lin and Jaysena, *J. Mol. Biol.* 271:100-11, 1997; Pavlov et al., *Trends in Biotechnol.* 22:253-60, 2004; and *Enzymatic Resource Guide: Polymerases*, 1998, Promega, Madison, Wis.

Detection

In various detection embodiments, amplification is optionally followed by additional steps, for example, but not limited to, labeling, sequencing, purification, isolation, hybridization, size resolution, expression, detecting and/or cloning. In certain embodiments, one or both PCR primers can comprise a label, such as, for example, a fluorophore. A label can facilitate detection of an amplification product comprising a labeled PCR primer. In some embodiments, detection is using intercalators (SYBR).

As used herein, "real-time PCR" refers to the detection and quantitation of a DNA or a surrogate thereof in a sample. In some embodiments, the amplified segment or "amplicon" can be detected in real time using a 5'-nuclease assay, particularly the TaqMan® assay as described by e.g., Holland et al. (*Proc. Natl. Acad. Sci. USA* 88:7276-7280, 1991); and Heid et al. (*Genome Research* 6:986-994, 1996). For use herein, a TaqMan® nucleotide sequence to which a TaqMan® probe binds can be designed into the primer portion, or known to be present in DNA of a sample.

In some embodiments, the PCR methods use end-point PCR and a positive result is obtained when there is a detectable signal after the PCR is finished. Real-time and end-point PCR methods useful in accordance with the present methods and compositions include, but are not limited to, fluorescence resonance energy transfer (FRET), TAQMAN®, Molecular Beacons, Amplifluor®, Scorpion™, Plexor™, BHQplus™.

When a TaqMan® probe is hybridized to DNA or a surrogate thereof, the 5'-exonuclease activity of a thermostable DNA-dependent DNA polymerase such as SUPERTAQ® (a Taq polymerase from *Thermus aquaticus*, Ambion, Austin, Tex.) digests the hybridized TaqMan® probe during the elongation cycle, separating the fluor from the quencher. The reporter fluor dye is then free from the quenching effect of the quencher moiety resulting in a decrease in FRET and an increase in emission of fluorescence from the fluorescent reporter dye. One molecule of reporter dye is generated for each new molecule synthesized, and detection of the free reporter dye provides the basis for quantitative interpretation of the data. In real-time PCR, the amount of fluorescent signal is monitored with each cycle of PCR. Once the signal reaches a detectable level, it has reached the "threshold or cycle threshold (Ct)." A fluorogenic PCR signal of a sample can be considered to be above background if its Ct value is at least 1 cycle less than that of a no-template control sample. The term "Ct" represents the PCR cycle number when the signal is first recorded as statistically significant. Thus, the lower the Ct value, the greater the concentration of nucleic acid target. In the TaqMan® assay, typically each cycle almost doubles the amount of PCR product and therefore, the fluorescent signal should double if there is no inhibition of the reaction and the reaction was nearly 100% efficient with purified nucleic acid. Certain systems such as the ABI 7500, 7500FAST, 7700 and 7900HT Sequence Detection Systems (Applied Biosystems, Foster City, Calif.) conduct monitoring during each thermal cycle at a pre-determined or user-defined point.

Detection method embodiments using a TaqMan® probe sequence comprise combining the test sample with PCR reagents, including a primer set having a forward primer and a reverse primer, a DNA polymerase, and a fluorescent detector oligonucleotide TaqMan® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

Protocols and reagents for means of carrying out other 5'-nuclease assays are well known to one of skill in the art, and are described in various sources. For example, 5'-nuclease reactions and probes are described in U.S. Pat. No. 6,214,979 issued Apr. 10, 2001; U.S. Pat. No. 5,804,375 issued Sep. 8, 1998; U.S. Pat. No. 5,487,972 issued Jan. 30, 1996; and 5,210,015 issued May 11, 1993, all to Gelfand et al.

"$T_m$" refers to the melting temperature (temperature at which 50% of the oligonucleotide is a duplex) of an oligonucleotide determined experimentally or calculated using the nearest-neighbor thermodynamic values of SantaLucia J. et al. (*Biochemistry* 35:3555-62, 1996) for DNA. In general, the $T_m$ of the TaqMan® probe is about 10 degrees above the $T_m$ of amplification primer pairs. The $T_m$ of the MGB probes is calculated using the SantaLucia method with factors correcting for the increased $T_m$ due to MGB.

As used herein, the term "Ct" represents the PCR cycle number when the signal is first recorded as statistically significant. The term "Cq" designates quantification cycle and is interchangeable with the term "Ct" (See e.g., "MIQE: Minimum Information for Publication of Quantitative Real-Time PCR Experiments," *Clinical Chemistry* 55:4; 611-622 (2009).

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context. The term "surrogate" as used herein means a product that is indicative of presence of another product. For example, an amplification product is a surrogate for a nucleic acid that has been amplified.

As used herein, "amplification" or "amplify" and the like refers to a process that results in an increase in the copy number of a molecule or set of related molecules. Amplification can encompass a variety of chemical and enzymatic processes including without limitation, a polymerase chain reaction (PCR), a strand displacement amplification reaction, a transcription mediated amplification reaction, a nucleic acid sequence-based amplification reaction, a rolling circle amplification reaction, or a ligase chain reaction. According to certain embodiments, following at least one amplification cycle, the amplification products can be detected by sequence or by separation based on their molecular weight or length or mobility, for example.

The term "end-point" measurement refers to a method where data collection occurs only once the reaction has been stopped.

The term "real-time" and "real-time continuous" are interchangeable and refer to a method where data collection occurs through periodic monitoring during the course of the polymerization reaction. Thus, the methods combine amplification and detection into a single step.

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

As used herein, the term "nucleotide" or "nt" refers to a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, 7-deaza-dGTP and 7-deaza-dATP. The term nucleotide as used herein also refers to dideoxyribonucleoside triphosphates (ddNTPs) and their derivatives. Examples of dideoxyribonucleoside triphosphates include, but are not limited to, ddATP, ddCTP, ddGTP, ddITP, and ddTTP.

As used herein, the phrase "nucleic acid molecule" refers to a sequence of contiguous nucleotides (riboNTPs, dNTPs or ddNTPs, or combinations thereof) of any length which can encode a full-length polypeptide or a fragment of any length thereof, or which can be non-coding. As used herein, the terms "nucleic acid molecule" and "polynucleotide" can be used interchangeably and include both RNA and DNA.

As used herein, the term "oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

The term "zpcr score" refers to values that score the mismatches of a TaqMan® assay against DNA sequences. The scoring matrix uses position and type of mismatch. Higher numbers indicate a low predicted hybridization of the assay to a DNA sequences, low numbers indicate a high chance of hybridization. 0 indicates a perfect match meaning the oligo will hybridize.

Labels

A "label" or "reporter," refers to a moiety or property that allows the detection of that with which it is associated. The label can be attached covalently or non-covalently. Examples of labels include fluorescent labels (including, e.g., quenchers or absorbers), colorimetric labels, intercolators, chemiluminescent labels, bioluminescent labels, radioactive labels, mass-modifying groups, antibodies, antigens, biotin, haptens, enzymes (including, e.g., peroxidase, phosphatase, etc.), and the like. Fluorescent labels can include dyes that are negatively charged, such as dyes of the fluorescein family including, e.g. FAM™ dye, HEX™ dye, TET™ dye, JOE™ dye, NAN and ZOE; or dyes that are neutral in charge, such as dyes of the rhodamine family including, e.g., TEXAS RED® dye, ROX™ dye, R110, R6G, and TAMRA™ dye; or dyes that are positively charged, such as dyes of the CYANINE™ family including e.g., Cy™2 dye, Cy™3 dye, Cy™5 dye, Cy®5.5 dye and Cy™7 dye. FAM™ dye, HEX™ dye, TET™ dye, JOE™ dye, NAN, ZOE, ROX™ dye, R110, R6G, and TAMRA™ dyes are available from, e.g., Applied Biosystems (Foster City, Calif.) or Perkin-Elmer, Inc. (Wellesley, Mass.); TEXAS RED® dye is available from, e.g., Molecular Probes, Inc. (Eugene, Oreg.); and Cy™2 dye, Cy™3 dye, Cy™5 dye, Cy™5.5 dye and Cy™7 dye, and are available from, e.g., Amersham Biosciences Corp. (Piscataway, N.J.). In certain embodiments, the fluorescent molecule is a fluorescein dye and the quencher molecule is a rhodamine dye.

A label or reporter can comprise both a fluorophore and a fluorescence quencher. The fluorescence quencher can be a fluorescent fluorescence quencher, such as the fluorophore TAMRA™ dye, or a non-fluorescent fluorescence quencher (NFQ), for example, a combined NFQ-minor groove binder (MGB) such as an MGB ECLIPSE™ minor groove binder supplied by Epoch Biosciences (Bothell, Wash.) and used with TaqMan® probes (Applied Biosystems, Foster City, Calif.). The fluorophore can be any fluorophore that can be attached to a nucleic acid, such as, for example, FAM™ dye, HEX™ dye, TET™ dye, JOE™ dye, NAN, ZOE, TEXAS RED® dye, ROX™ dye, R110, R6G, TAMRA™ dye, Cy™2 dye, Cy™3 dye, Cy™5 dye, Cy™5.5 dye and Cy™7 dye as cited above as well as VIC® dye, NED™ dye, LIZ® dye, ALEXA, Cy™9 dye, and dR6G.

Further examples of labels include black hole quenchers (BHQ) (Biosearch), Iowa Black (IDT), QSY quencher (Molecular Probes), and Dabsyl and Dabcel sulfonate/carboxylate Quenchers (Epoch).

Labels can also comprise sulfonate derivatives of fluorescein dyes, phosphoramidite forms of fluorescein, phosphoramidite forms of CY™5 (available for example from Amersham), intercalating labels such as ethidium bromide, and SYBR™ Green I dye and PICOGREEN™ dye (Molecular Probes). Generally, an intercalating label is a molecule that reversibly inserts between two other molecules (or groups) such as between the bases of DNA.

In various embodiments, qPCR reactions can include master mixes such as the TaqMan® Environmental Master Mix, TaqMan® Gene Expression Master Mix, TaqMan® Universal PCR Master Mix, TaqMan® Fast Universal PCR Master Mix, Power SYBR® Green PCR Master Mix, Fast SYBR® Green Master Mix, for example, all from Applied Biosystems.

In various embodiments, detection of fluorescence of a PCR assay can be by any method known to skilled artisans, and can include, for example, real time detection as described supra or end point detection. Detection of fluorescence can be qualitative or quantitative. Quantitative results can be obtained, for example, with the aid of a fluorimeter, for example a fluorimeter comprised by an integrated nucleic acid analysis system, such as, for example, an Applied Biosystems ABI PRISM™ 7900HT Sequence Detection System. Furthermore, quantitative results can be obtained in some configurations using a real-time PCR analysis as described supra. Some non-limiting examples of protocols for conducting fluorogenic assays such as TaqMan® assays, including analytical methods for performing quantitative assays, can be found in publications such as, for example, "SNPLEX™ Genotyping System 48-plex", Applied Biosystems, 2004; "User Bulletin #2 ABI PRISM™ 7700 Sequence Detection System," Applied Biosystems 2001; "User Bulletin #5 ABI PRISM™ 7700 Sequence Detection System," Applied Biosystems, 2001; and "Essentials of Real Time PCR," Applied Biosystems (Foster City, Calif.). Fluorogenic PCR assays used in some configurations of the present teachings can be performed using an automated system, such as, for example, an ABI 7700 Sequence Detection System (Applied Biosystems).

For real time PCR, a passive reference dye, ROX™ dye, can be included in PCR reactions to provide an internal reference to which the reporter-dye signal can be normalized during data analysis. Normalization can be accomplished using Applied Biosystems' Sequence Detection System (SDS) software.

In general for the studies herein, the TaqMan® probes were labeled with FAM™ dye, the TaqMan® probe for the Internal Positive Control was labeled with VIC® dye. Data analyses were carried out using the RAPIDFINDER™ Express Software (Applied Biosystems) and results are provided in an easy-to-read format with present/absent calls.

The primer sets provided herein for detection of *S. Enteritidis* can be termed a "*S. Enteritidis*-specific" primer set since the set provides for detection of *S. Enteritidis* without cross-reacting with *S. Paratyphi* C and other *Salmonella* species.

Kits

A "kit," as used herein, refers to a combination of at least some items for performing a PCR assay for *S. Enteritidis* detection. Embodiments of kits may comprise one or more of the following reagents: at least one set of primers specific for *S. Enteritidis* detection, at least one probe specific for *S. Enteritidis* detection, internal positive control DNA to monitor presence of PCR inhibitors from various food and environmental sources, a baseline control, reagents for sample collection, reagents for isolating nucleic acid such as magnetic beads, spin columns, lysis buffers, proteases, reagents for PCR amplification such as a DNA polymerase or an enzymatically active mutant or variant thereof, a DNA polymerase buffer, deoxyribonucleotides dATP, dCTP, dGTP, or dTTP. In some embodiments, a probe is a TaqMan® probe. In certain kit embodiments, amplification primers are attached to a solid support such as a microarray. In some embodiments, a kit may include an internal control (a *Salmonella* control) such as primers and probes specific for the invA gene.

One or more kit components may be packaged in one or more container means. Kit container means may generally include at least one vial, test tube, flask, bottle, syringe or other packaging means, into which a component can be placed, and in some embodiments, suitably aliquoted. Where more than one component is included in a kit (they can be packaged together), the kit also will generally contain at least one second, third or other additional container into which the additional components can be separately placed. However, various combinations of components can be packaged in a container means. Kits of the present teachings also will typically include reagent containers in close confinement for commercial sale. Such containers can include injection or blow-molded plastic containers into which the desired container means are retained. When the components of kits are provided in one and/or more liquid solutions, the liquid solution comprises an aqueous solution that can be a sterile aqueous solution.

In certain embodiments, at least one kit component is lyophilized and provided as dried powder(s). For example, primers and TaqMan® probes may be lyophilized. When reagents and/or components are provided as a dry powder, the powder can be reconstituted by the addition of a suitable solvent. In certain embodiments, a solvent is provided in another container means. Kits can also comprise an additional container means for containing a sterile, pharmaceutically acceptable buffer and/or other diluent.

A kit can also include instructions for employing the kit components as well as the use of any other reagent not included in the kit. Instructions can include variations that can be implemented.

In some embodiments, a kit may contain reagents for between 1 and 1000 Real-time PCR reactions, including but not limited to, a *S. Enteritidis* FAM™-dye labeled probe, and an Internal Positive Control (IPC) VIC®-dye labeled probe. Environmental Master mix can contain the hot-start enzyme AmpliTaq Gold LD for easy handling, a nucleotide mix and optimized buffer components to compensate for low levels of PCR-inhibitors introduced by the sample matrix. A kit can also include a negative control to monitor for contamination and reagent integrity.

An exemplary kit may comprise one or more compositions for detecting one or more *S. Enteritidis* may comprise at least one primer pair having hybridization specificity for amplifying a Prot6e gene or a fragment thereof specific to *S. Enteritidis*.

An example kit for detecting *S. Enteritidis* may comprise at least one primer pair selected from a first primer pair having SEQ ID NO:1 and SEQ ID NO:3, or a second primer pair having SEQ ID NO:4 and SEQ ID NO:6, or a third primer pair having SEQ ID NO:7 and SEQ ID NO:9, or a fourth primer pair having SEQ ID NO:10 and SEQ ID NO:12, or a fifth primer pair having SEQ ID NO:13 and SEQ ID NO:15, or a primer pair having nucleic acid molecules with at least 90% sequence homology to the primer pair sequences, and/or a labeled derivatives thereof; wherein the primer pairs are operable to amplify a Prot6e gene of *S. Enteritidis* or a fragment thereof.

This kit embodiment may further comprise an isolated nucleic acid molecule having at least one probe selected from a first probe having SEQ ID NO:2, a second probe having SEQ ID NO:5, a third probe having SEQ ID NO:8, a fourth probe having SEQ ID NO:11, and a fifth probe having SEQ ID NO:14, wherein each of these probes may be used to detect amplification products generated by the primer pairs described in the paragraph above respectively. In some embodiments, probe sequences may have at least 90% sequence homology to said probe sequences, and maybe labeled derivatives thereof.

Some kit embodiments, may comprise primer pairs having hybridization specificity for amplifying a Prot6e gene or fragment thereof only found in *S. Enteritidis* and not in *S. Paratyphi* C, and may comprise at least one primer pair selected from a first primer pair having SEQ ID NO:1 and SEQ ID NO:3, or a second primer pair having SEQ ID NO:10 and SEQ ID NO:12, or a third primer pair having SEQ ID NO:13 and SEQ ID NO:15, or a primer pair having nucleic acid molecules with at least 90% sequence homology to the primer pair sequences. This kit may further comprise at least one probe selected from a first probe having SEQ ID NO:2, a second probe having SEQ ID NO:11, and a third probe having SEQ ID NO:14, wherein each of these probes may respectively be used to detect amplification products generated by the primer pairs described above. In some embodiments, probe sequences may have at least 90% sequence homology to said probe sequences, and maybe labeled derivatives thereof.

In some embodiments a kit of the disclosure may comprise primer pairs (and optionally corresponding probes) for a duplexed or multiplexed assay as described in embodiments above.

In some embodiments, a kit of the disclosure may be created by lyophilizing reagents for a real-time PCR assay (such as primer sequences and optionally probe sequences) together with reagents of a PCR master mix. Kits having these features provide a convenient format since use of such a kit merely requires the addition of sample to the lyophilized kit reagent. Accordingly, in some embodiments, each assay (combination of primer pairs and optionally probes are described as Assay Id No. in Table 2) may be developed into a kit of the disclosure.

EXAMPLES

Aspects of the present teachings can be further understood in light of the following examples, which should not be construed as limiting the scope of the present teachings in any way.

Example 1

Primer/Probe Sets for Specific Detection of *S. Enteritidis* that do not Cross-React with *S. Paratyphi* C A *S. Enteritidis* TaqMan® assay for targeting the plasmid-borne Prot6e gene was described by Malorney, et al. (Journal of Microbiological Methods, 70 (2007) 245-251). This assay was developed and tested on 79 *S. Enteritidis* strains and 119 non-nteritidis *Salmonella* strains belonging to 59 other serotypes. The assay was reported to detect the Prot6e gene in *S. Enteritidis* containing the Prot6e gene and did not cross-react with the 119 other *Salmonella* strains tested. Malorney assays and probe and primer sequences are shown as Assay ID 27293 in Table 1, where the term "FWDSEQ" represents the sequence of a forward primer, the term "REVSEQ" represents the sequence of a reverse primer, and the term "PROBESEQ" represents the sequence of a probe. Additional assays using the same forward and reverse primers that Malorney published, but different probes are also presented in Table 1. The probes were designed to use the minor grove binding protein (MGB).

However, the *S. Paratyphi* C strain was not tested by Malorney et al., and subsequent analysis of the primers and probes used by Malorney et al. suggested they would cross-react with *S. Paratyphi* C. Using a bioinformatic approach, a sequence analysis of the *S. Enteritidis* primers used in the Malorney et al. assays compared to the *S. Paratyphi* C gene showed a zpcr score of 70. A zpcr score of 250 or less suggests that a primer or probe will cross-react with the strain analyzed. Thus, the Malorney assays could cross-react with *S. Paratyphi* and result in false positives when using the assay to identify *S. Enteritidis*. This cross-reactivity was subsequently confirmed in laboratory experiments.

In order to eliminate cross-reactivity of the Malorney assay with *S. Paratyphi* C, three MGB derivatives of the original probe were designed (assay IDs 27329, 27334, and 27335 in Table 1). These gave slightly better predicted discrimination, but the zpcr score of 90 for *S. Paratyphi* C was not sufficiently high to inhibit cross-reactivity.

Table 2 provides probe and primer sequences that were designed in the present disclosure for the detection of *S. Enteritidis*. In the tables, the term "FWDSEQ" represents the sequence of a forward primer, the term "REVSEQ" represents the sequence of a reverse primer, and the term "PROBESEQ" represents the sequence of a probe (which in some embodiments may be a TaqMan® probe).

TABLE 1

Minor Groove Binder (MGB) probe derivatives of Malorney, et al., assay targeting the Prot6e gene (Malorney et al. Journal of Microbiological Methods, 70 (2007) 245-251).

| Assay ID | FWDSEQ | PROBESEQ | REVSEQ | For Tm | Probe Tm | Rev Tm |
|---|---|---|---|---|---|---|
| 27329 | ATATCGTCGTTGC TGCTTCC (SEQ ID NO: 16) | TCGGTCCTGCTGTAG ATGC (SEQ ID NO: 17) | CATTGTTCCACCGTC ACTTTG (SEQ ID NO: 18) | 60.4 | 72.54 | 59.76 |
| 27334 | ATATCGTCGTTGC TGCTTCC (SEQ ID NO: 16) | ATCGGTCCTGCTGTA GATGC (SEQ ID NO: 19) | CATTGTTCCACCGTC ACTTTG (SEQ ID NO: 18) | 60.4 | 73.01 | 59.76 |
| 27335 | ATATCGTCGTTGC TGCTTCC (SEQ ID NO: 16) | CTCATCGGTCCTGCT GTAGAT (SEQ ID NO: 20) | CATTGTTCCACCGTC ACTTTG (SEQ ID NO: 18) | 60.4 | 71.43 | 59.76 |
| 27293 | ATATCGTCGTTGC TGCTTCC (SEQ ID NO: 16) | AGGCGCTCATCGGT CCTGCTGT (SEQ ID NO: -21) | CATTGTTCCACCGTC ACTTTG (SEQ ID NO: 18 | — | — | — |

TABLE 2

SE-specific assays targeting the Prot6e gene

| Assay ID. | FWDSEQ | PROBESEQ | REVSEQ | For Tm | Probe Tm | Rev Tm |
|---|---|---|---|---|---|---|
| 27316 | AGGGCGAGGTTTGAA CCAA (SEQ ID NO: 1) | ATGCTCAGCTG CTCCAC (SEQ ID NO: 2) | GGATTCCCATAGCT GTAGCTTTGTT (SEQ ID NO: 3) | 61.77 | 69.07 | 62.27 |
| 27317 | GCAGTGTACAGGGCA AAATAGCAATA (SEQ ID NO: 4) | CCCATCTCAAA AATCT (SEQ ID NO: 5) | GGTAGAAATCGCCG TACACGAG (SEQ ID NO: 6) | 63.03 | 69.79 | 62.66 |
| 27318 | AGTGTGGTGACCCCCA TCT (SEQ ID NO: 7) | TCGCCGTACAC GAGCTT (SEQ ID NO: 8) | AAACCTCGCCCTCA CATTCA (SEQ ID NO: 9) | 62.51 | 70.79 | 61.65 |

TABLE 2-continued

SE-specific assays targeting the Prot6e gene

| Assay ID. | FWDSEQ | PROBESEQ | REVSEQ | For Tm | Probe Tm | Rev Tm |
|---|---|---|---|---|---|---|
| 27319 | TTTATGAATGTGAGGG CGAGGTTT (SEQ ID NO: 10) | ATGCTCAGCTG CTCCAC (SEQ ID NO: 11) | AGGATTCCCATAGC TGTAGCTTTG (SEQ ID NO: 12) | 62.09 | 69.07 | 61.72 |
| 27320 | AGGTTTGAACCAAGTG GAGCA (SEQ ID NO: 13) | AAACAACGCGA ACCATG (SEQ ID NO: 14) | CCACTGACAGGATT CCCATAGC (SEQ ID NO: 15) | 61.91 | 69.77 | 62.1 |

In order to improve specificity for the *S. Enteritidis* serovar versus *S. Paratyphi* C, five new TaqMan® assays (identified in Table 2 by Assay ID. 27316-27320) were designed against a different region of Prot6e that is conserved in the two published *S. Enteritidis* sequences, but diverges significantly from the published *S. Paratyphi* C sequence. These assays were designed using an assay design pipeline, which generates candidate assay designs, and then screens these assays against inclusion and exclusion sequences in order to maximize inclusivity and exclusivity. Combinations of primers and probes were prepared for *S. Enteritidis* that had a zpcr score for *S. Paratyphi* C of greater than 250. Thus, these primers were chosen so that they would not cross-react with *S. Paratyphi* C. As shown in Table 3, the assays had zpcr scores of from 192 to greater than 300 for *S. Paratyphi* C. Thus, all of the primers and probes developed herein showed a better zpcr score than the Maloney assay.

Matching of these assays against the *S. Paratyphi* C sequence demonstrated improved predicted specificity for *S. Enteritidis*, with 3/5 assays (27316, 27319, and 27320) having a zpcr score greater than 250, which is predicted to be sufficient to block detection of *S. Paratyphi* C. All of these assays perfectly matched both *S. Enteritidis* sequences, and did not match any other microbial or human sequences in GenBank with a zpcr score of 250 or less. Thus, these primers show a very high degree of specificity for *S. Enteritidis* and should not result in cross-reactivity with *S. Paratyphi*.

Table 3 and FIG. 1 show results of analysis of primers/probes and zpcr score using bioinformatics. Using bioinformatic comparisons, the portions of the sequence of the Prot6e gene was found in common between *S. Enteritidis* and *S. Paratyphi* C and variable sequence regions were identified. FIG. 1 provides an alignment of oligonucleotides to the Prot6e target region. The top line is *S. Paratyphi* C (GenBank Accession No. CP000858.1), and the bottom two lines are *S. Enteritidis* (GenBank Accession Nos. U66901.1 and AB041905.1). Black bars at the bottom indicate conservation. The areas used for primers and probes are shown by assay ID numbers shown in Table 2. The map positions for the primers and accession numbers used in assays 27316-27320 map about 400 nucleotides upstream of the primers from Malorney et al. (assay ID 27293) and are provided in Table 8 below.

Table 3 shows the amplicon length for *S. Enteritidis* in the second column (Amp length) and for *S. paratyphi* C in the fifth column (Amp length). For example, using the primers and probes for assay ID 27316, the amplicon length for *S. Paratyphi* C was 136 and the amplicon length for *S. Enteritidis* was 83. The assays that showed the least cross-reactivity to *S. Paratyphi* C were 27320, 27319, and 27316.

TABLE 3

Off-target matching of proprietary assays.

| Assay ID | Amp length | Top off target hit: Organism | zper score | Amp length | Top human hit |
|---|---|---|---|---|---|
| 27320 | 86 | | >300 | | >300 |
| 27316 | 83 | *S. Paratyphi* C | 270 | 136 | >300 |
| 27317 | 86 | *S. Paratyphi* C | 192 | 86 | >300 |
| 27318 | 87 | *S. Paratyphi* C | 213 | 393 | >300 |
| 27319 | 96 | | >300 | | >300 |

Thus, primers and probes were produced to provide a more specific assay for detecting the presence of *S. Enteritidis* that does not cross-react with *S. Paratyphi* C.

Example 2

Assays for Detection of *S. Enteritidis* that do not Cross-React with *S. Paratyphi* C To test the results experimentally, the primers and probes from Example 1 were used in a TaqMan® assay to identify *S. Enteritidis*. The PCR amplification primers and TaqMan® assays drawn against the Prot6e sequences were designated assay number 27316, 27317, 27318, 27319, and 27320. The Malorney assays and MGB-probe derivatives were designated 27329, 27293, 27334, and 27335 (See Tables 1 and 2). The probes were labeled with 6-FAM and an Eclipse Dark Quencher.

For *S. Enteritidis*-specific assay 27316, PCR amplification primers and a TaqMan® probe assays were produced using the primers SEQ ID NO:1 and SEQ ID NO:3 and the probe SEQ ID NO:2 and designated assay no. 27316 (See Tables 2 and 3). The amplicon size was 83 nucleotides, the predicted melting temperatures of the forward primer, reverse primer and probe were 61.77° C., 62.27° C., and 69.07° C., respectively.

For *S. Enteritidis*-specific assay 27319, PCR amplification primers and a TaqMan® probe assays were produced using the primers SEQ ID NO:10 and SEQ ID NO:12 and the probe SEQ ID NO:11 and designated assay no. 27319 (See Tables 2 and 3). The amplicon size was 96 nucleotides, the predicted melting temperatures of the forward primer, reverse primer and probe were 62.09° C., 61.72° C., and 69.07° C., respectively.

For *S. Enteritidis*-specific assay 27320, PCR amplification primers and a TaqMan® probe assays were produced using the primers SEQ ID NO:13 and SEQ ID NO:15 and the probe SEQ ID NO:14 and designated assay no. 27320 (See Tables 2 and 3). The amplicon size was 86 nucleotides, the predicted melting temperatures of the forward primer, reverse primer and probe were 61.91° C., 62.1° C., and 69.77° C., respectively.

DNA sequence alignment analyses confirmed that each of these primers and probes had a perfect match in *S. Enteritidis* sequences. Alignment of this combination of oligonucleotides against the microbial subset of the GenBank database did not reveal any significant matches to organisms other than *S. Enteritidis*.

Table 4 provides a summary of the TaqMan® assay data using the above-cited primer/probe set on several *S. Enteritidis* isolates.

Briefly, Real-Time PCR assay mixes were prepared for the five assays (27293, 27316, 27319, 27320, and 27329) and for the Malorney assays (27329, 27393, 27334 and 27335) to create a final assay mixture containing 900 nM primer concentration and 250 nM probe concentration. Each assay mixture also contained Internal Positive Control (IPC) primers and probe at concentrations of 450 nM and 125 nM, respectively; and IPC template at (10× concentration, Applied Biosystems). The final assay mix represents a 10× mixture. *S. Enteritidis* (PE18), *S. Enteritidis* (PE19), *S. Paratyphi* C (PE223), and *S. Infantis* (PE7) were enriched overnight at 37° C. in 5 mL of Brain Heart Infusion (BHI) broth, and sample DNA was prepared using the PrepSEQ™ Rapid Spin Sample Preparation Kit (Applied Biosystems). Real-Time PCR reaction mixes were prepared by combining 15 µL of 2× Environmental Master Mix version 2 (EMM v.2), 3 µL of 10× Assay Mix, 5 µL of sample DNA, and 7 µL of PCR-clean water for a final volume of 30 µL. Real-Time PCR was run on the 7500 Fast instrument using the following cycling conditions: 95° C. for 10 min for 1 cycle; 95° C. for 15 seconds and 60° C. for 60 seconds for 40 cycles. Results were analyzed on SDS version 1.4.1 software using default instrument settings. Positive amplification signal was reported as Ct values (cycle threshold: the cycle number at which amplification crosses the threshold). Samples that were not detected by Real-Time PCR were reported as undetermined (un). NTC is negative template control and was run in the absence of sample DNA (water was substituted for sample DNA in the reaction mix).

TABLE 4

Threshold cycle (Ct) values for selected assays.

| Assay ID | Source | NTC | Enteritidis PE18 | Enteritidis PE19 | Paratyphi C PE223 | Infantis PE7 |
|---|---|---|---|---|---|---|
| 27293 | Malorney | un | 23.43 | 21.76 | 22.99 | un |
| 27316 | proprietary | un | 23.01 | 21.30 | un | un |
| 27319 | proprietary | un | 23.10 | 21.40 | un | un |
| 27320 | proprietary | un | 23.45 | 21.54 | un | un |
| 27329 | Malorney derivative | un | 22.80 | 21.51 | 27.26 | un | un—undetermined, i.e., the amplification signal did not cross the threshold of detection before the end of the run (typically 40 PCR cycles).

The results showed that the Malorney primers cross-reacted with *S. paratyphi* C and the primers of the present disclosure did not. All of the primers showed no reaction with *S. Infantis* (as expected). NTC is the non-template control and did not show any detection. The values in Table 4 (e.g., 23.43) are the number of amplification cycles that were required to get a detectable result. A number greater than 40 is designated "un" (undetermined) meaning that nothing was amplified over the course of the 40-cycle amplification protocol. Thus, while the Malorney assays and the new assays were comparable to one another in the detection of *S. Enteritidis*, the Malorney assays also detected *S. Paratyphi* C while the assays of the present disclosure (Assay IDs 27316, 27319 and 27320) did not. Accordingly, assays 27316, 27319 and 27320 were *S. Enteritidis*-specific assays.

Example 3

Detection of *S. Enteritidis* (SE) in Egg Pools and Environmental Drag Swabs

The duplexed TaqMan® assay of Example 2 was evaluated for detection of *S. Enteritidis* from egg samples. The assay was performed as follows:

Bacterial Growth and Sample Enrichment Conditions: Bacteria were routinely cultured on Brain Heart Infusion (BHI) Agar plate and BHI broth at 37° C. overnight. Bacteria were spiked in the 1-10 colony forming unit (cfu) range.

Egg Testing: For egg testing, egg pool samples were prepared as described in the FDA's Bacteriological Analytical Manual (BAM), chapter 5, December 2007 Edition (2). Each egg pool held the contents of 20 individual eggs. Egg samples were enriched by the short enrichment protocol as follows:

Short Enrichment Protocol: 0.1 volume (±20%) of 10×TS broth was added to each egg pool (i.e. ~100 mL of 10×TSB to ~1 liter of eggs). The samples were mixed by swirling until the broth was homogeneously dispersed amongst the egg pool sample. The samples were incubated at 35±2° C. for 24±2 hours. Samples were prepared as discussed below (Sample preparation A, B, or C was used). Samples were confirmed to be positive or negative based on culture results.

Alternatively, the samples could also be enriched by one of the following standard enrichment protocols (4 day or 5 day protocols): The 4 day protocol was as follows: The egg pool samples were incubated at room temperature for 96 hr and then the sample was prepared as discussed below. The 5 day protocol was as follows: The egg pool samples were incubated at room temperature for 96 hours. 25 mL of the test portion was transferred to 225 mL of trypticase soy broth supplemented with ferrous sulfate (mTSB; 35 mg ferrous sulfate/liter broth). The samples were mixed by swirling until the broth is homogenously dispersed amongst the egg pool sample. The egg pool samples were incubated for 1 hour at room temperature. The pH was adjusted to 6.8±0.2 with 1 N HCl or 1 N NaOH. The egg pool samples were incubated for 24 hours at 35±2° C. The samples were prepared as discussed below (Sample preparation A or B was used).

Environmental Drag Swab Testing: Environmental sampling and preparation followed the guidelines outlined in the U.S. FDA protocol entitled, Environmental Sampling and Detection of *Salmonella* in Poultry Houses, October 2008 Edition (3). Manure was the preferred sample type. Swab testing was performed as follows: A 10 cm×10 cm (4 in×4 in) 12 ply sterile gauze pad was used which was aseptically attached to a pole by clips or to a string. A pad was moistened with canned evaporated milk, canned skim (fat free) evaporated milk, or canned low fat evaporated milk. The moistened gauze pad was dragged over the manure the entire length of one side of row/bank. Another gauze pad was taken and dragged across the other side of the row/bank. This procedure was repeated on all rows/banks of the house. Each drag swab was placed into a separate whirl-pak bag with sufficient milk to keep the pad wet (no more than a tablespoon or approximately 15 ml).

The environmental samples were enriched as follows: 100 mL to 150 mL of Tetrathionate Broth (TT Broth) was added to the whirl-pak bag containing the environmental gauze pad to a ratio of 1:9 sample to broth. The bag was shaken vigorously in an up-and-down motion at least 10 times in a 30 cm (1 ft) arc in approximately 30 sec. The bag was incubated at 35±2° C. for 24±2 hours and sampled for the PrepSeq™ NA Extraction workflow. Sample preparation A or C was used.

Sample Preparation was using either method A (PrepSEQFA), B (PrepSEQFP) or C (PrepSEQGN). The methods were compared in Tables 5-7. The methods were performed as follows:

Sample preparation method A. PrepSEQFA—PrepSEQ™ Nucleic Acid Extraction—250 µl Lysis Protocol (4428176DWPrepSEQFA). Before samples were processed, a tube of magnetic particles was removed from storage at 4° C. and placed at 37° C. for 10 minutes and vortexed before use. Wash and Elution Plates were prepared and pre-loaded on a MagMAX™ Express-96 Magnetic Particle Processor (MME-96 instrument) up to 30 minutes prior to sample collection.

The reagent plates were prepared as follows: Lysis Plate: 250 µL of Lysis Buffer was added to as many wells of a MagMAX™ Express-96 Deep-Well plate that there were samples to be analyzed, plus one for buffer control (BC). Elution Plate: 100 µL of Elution Buffer was added to each well of a MagMAX™ Express-96 standard plate that correspond to those wells that contained sample in the Lysis Plate. Wash Plate: 2 identical Wash Plates were prepared in MagMAX™ Express-96 Deep-well plates by adding 300 µL of Wash Buffer to well positions that contained elution buffer in the elution plate. Tip Combs: A tip comb was placed in a MagMAX™ Express-96 standard plate.

Enriched samples were collected from the incubator and the whirl-pak bags briefly shaken to mix the sample. 250 µL of sample was transferred into the Lysis Plate containing 250 µL of Lysis Buffer. The Magnetic Particles were vortexed for 5 seconds until resuspension was complete. 30 µL of the Magnetic Particles was added to each well. 300 µL of Binding Solution was added to each well. Plates were loaded into the MagMax™ Express-96 instrument and run. When the sample preparation was complete, the Elution Plate was retrieved and the sample was used immediately for Real-Time PCR, or stored at −20 C.

B. PrepSEQPK—PrepSEQ™ Nucleic Acid Extraction—250 µL Lysis Protocol with PK (4428176DWPrepSEQFP) was performed as follows: Before samples were processed, a tube of magnetic particles was removed from storage at 4° C. and placed at 37° C. for 10 minutes and vortexed before use. Elution Plates were washed and prepared and pre-loaded on the MME-96 instrument up to 30 minutes prior to sample collection. The reagent plates were prepared as follows: Lysis Plate: 140 µL of Proteinase K Buffer and 10 µL of Proteinase K was added to as many wells of a MagMAX™ Express-96 Deep-Well plate that there were samples to be analyzed, plus one for buffer control (BC). Elution Plate: 100 µL of Elution Buffer was added to each well of a MagMAX™ Express-96 standard plate that corresponded to those wells that contained sample in the Lysis Plate. Wash Plate: 2 identical Wash Plates were prepared in MagMAX™ Express-96 Deep-well plates by adding 300 µL of Wash Buffer to well positions that contained elution buffer in the elution plate. Tip Combs: Tip combs were placed in a MagMAX™ Express-96 standard plate. The enriched samples were collected from the incubator and the whirl-pak bags were briefly shaken to mix the sample. 250 µL of sample was transferred into the Lysis Plate containing 150 µL of Proteinase K mix. The plates were loaded into the MagMax™ Express-96 instrument and run. The MagMAX™ Express-96 Magnetic Particle Processor was switched on and program 4428176DWPrepSEQFP was selected and started. The plates were loaded according to the instrument readout and orientation verified {A1 to A1} Tip combs—in standard 96-well plate and the Start was pressed. Elution plate (100 µL of Elution Buffer)—In standard 96-well plate and the Start was pressed. Wash plate 2 (300 µL of Wash Buffer)—In deep-well 96-well plate and the Start was pressed. Wash plate 1 (300 µL of Wash Buffer)—In deep-well 96-well plate and the Start was pressed. Lysis plate (sample in Lysis Buffer)—In deep-well 96-well plate and the Start was pressed. After 20 minutes, when the MagMax™ Express-96 magnetic particle processor prompted, the Lysis Plate was retrieved from the instrument. 250 µL of Lysis Buffer was added to each well containing sample, plus BC. The Magnetic Particles were vortexed for 5 seconds until resuspension was complete. 30 µL of the Magnetic Particles was added to each well containing sample, plus BC. 325 µL of Binding Solution was added to each well containing sample, plus BC. The Lysis Plate was loaded back into the instrument and Start was pressed. When the sample preparation was complete, the Elution Plate was removed and it was used immediately for Real-Time PCR, or stored at −20° C.

C. PrepSEQ™ Nucleic Acid Extraction—1 mL Lysis Protocol (PrepSEQGN) or Standard Protocol was performed as follows: Before samples were processed, a tube of magnetic particles was removed from storage at 4° C. and placed at 37° C. for 10 minutes and vortexed before use. The wash and Elution Plates were prepared and pre-loaded on the MME-96 instrument up to 30 minutes prior to sample collection. The reagent plates were prepared as follows: Elution Plate: 140 µL of Elution Buffer was added to each well of a MagMAX™ Express-96 standard plate that correspond to those wells that contain sample in the Lysis Plate, plus one extra well for buffer control (BC). Wash Plate: 2 identical Wash Plates were prepared in MagMAX™ Express-96 Deep-well plates by adding 300 µl of Wash Buffer to well positions that contain elution buffer in the elution plate. Tip Combs: The Tip comb was placed in a MagMAX™ Express-96 standard plate. The enriched samples were collected from the incubator and the whirl-pak bags were briefly shaken to mix the sample. 1 mL of sample was transferred into a labeled 1.5-mL microcentrifuge tube and centrifuged for 3 minutes at 16000×g. The supernatant was removed and discarded as quickly as possible to prevent dissipation of the pellet. (Note: If no pellet was observed, all but the last ~50 µL of supernatant was discarded so as to not disturb the bacteria pellet). 300 µL of Lysis Buffer was added to the tube. This was resuspended by pipetting up and down, or vortexed until the pellet was resuspended. The sample was transferred to a sterile 96-well deep well (DW) plate. The plates were loaded into the MagMax™ Express-96 instrument and the MagMAX™ Express-96 Magnetic Particle Processor was switched on. Program 44000799DWPrepSEQGN was selected and Start was pressed. The plates were loaded according to the instrument readout and the orientation was verified {A1 to A1}. Tip combs—in standard 96-well plate; and Start was pressed. Elution plate (140 µL of Elution Buffer)—In standard 96-well plate; and Start was pressed. Wash plate 2 (300 µL of Wash Buffer)—In deep-well 96-well plate; and Start was pressed. Wash plate 1 (300 µL of Wash Buffer)—In deep-well 96-well plate; and Start was pressed. Lysis plate (sample in Lysis Buffer)—In deep-well 96-well plate; and Start was pressed. After 18 minutes, the Binding Mix was dispensed as prompted by the MagMax™ Express-96 magnetic processor. The Lysis Plate was retrieved from the instrument. The Magnetic Particles were vortexed for 5 seconds until resuspension was complete. 30 µL of the Magnetic Particles were added to each well. 180 µL of Binding Solution was added to each well. The Lysis Plate was loaded back into the instrument and the start was pressed. When the sample preparation was complete, the Elution Plate was retrieved and the sample used immediately for Real-Time PCR, or stored at −20° C.

Tables 5-7 provide data for egg samples using the three different types of nucleic acid extraction methods (PrepSEQFP, PrepSEQFA, and PrepSEQGN—see above for methods) and comparison with BAM methods (US FDA Bacteriological Analytical Manual). Table 5 provides data for enrichment of 10×TSB for 24 hrs. Table 6 provides data for enrichment for 96 hours at room temperature. Table 7 provides data for enrichment for 96 hr at ambient temperature and, then 24 hr in TSB+ferrous sulfate (US FDA BAM). The results of the FDA BAM method are reported as "*Salmonella* spp." (presence) or "Not Detected" (absence). The Real-Time PCR results are reported as Ct values (FAM channel detects SE target, and VIC channel detects internal positive control as an indicator of successful PCR conditions). These tables show that the results from the methods used in Examples 1-3 are directly comparable to the US FDA Bacteriological Analytical Manual (BAM protocols). All samples that showed the presence of *Salmonella* spp. using the BAM protocol also gave a FAM Ct value for the Real-Time PCR methods indicating presence of SE and thus show 100% correlation between the methods developed herein and the BAM methods. The BAM protocol requires pre-enrichment, enrichment in selective media, plating, biochemical testing, and serological testing. The entire process can take 5 to 7 days for presumptive detection of *Salmonella*. The methods disclosed herein provide the same answer in 27 hours.

Figure 2:
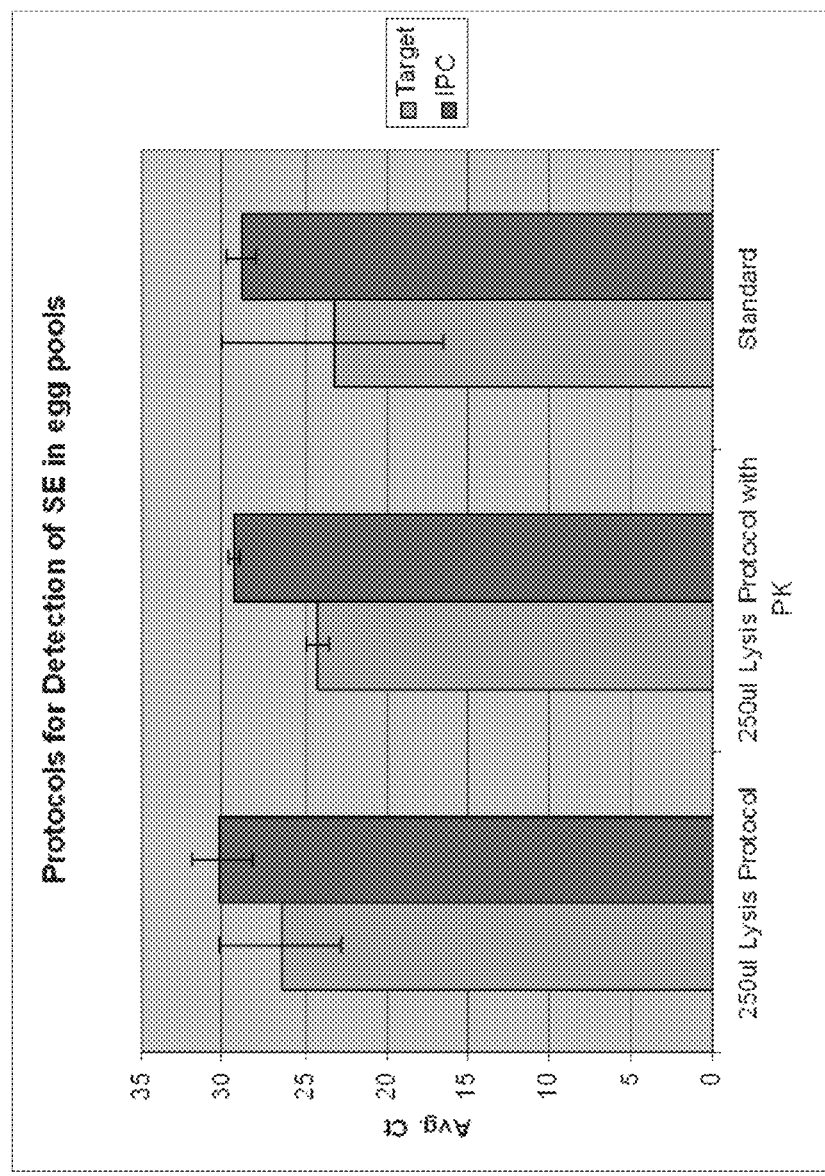
FIG. 2 shows the average Ct for the target and the internal positive control (IPC) using various protocols for the detection of S. Enteritidis in egg pools. The standard protocol refers to the PrepSEQ® Nucleic Acid Extraction Kit using the recommended method for detecting Salmonella in eggs (Life Technologies). All sample preparation was performed on the MagMax™ Express-96 Magnetic Particle Processor.

The results in FIG. 2 were generated using the short enrichment protocol. The Target was *S. Enteritidis* (FAM labeled), the IPC: Internal Positive Control was VIC labeled. The results demonstrated robust detection of *S. Enteritidis* by all 3 sample preparation methods tested. The IPC was minimally inhibited (VIC signal), indicating the sample preparation methods were efficient in removing PCR inhibitory components potentially present in the egg pools. Each data set was an average of 16 individual data points. The results demonstrated the robust assay sensitivity where *S. Enteritidis* was detected even by the simpler, short sample preparation methods (the 250 µl protocols) almost as well as the longer, standard protocol that uses 1 ml sample volumes.

TABLE 5

Enrichment: 10xTSB for 24 hr

| Sample Name | FDA BAM confirmed | PrepSEQFP | | PrepSEQFA | | PrepSEQGN | |
|---|---|---|---|---|---|---|---|
| | | FAM (SE) | VIC (IPC) | FAM (SE) | VIC (IPC) | FAM (SE) | VIC (IPC) |
| 1 | Not Detected | Undetermined | 28.8 | Undetermined | 30.0 | Undetermined | 28.8 |
| 2 | Not Detected | Undetermined | 28.7 | Undetermined | 29.9 | Undetermined | 28.7 |
| 3 | *Salmonella* sp. | 14.8 | 29.7 | 20.3 | 29.0 | 22.1 | 27.3 |
| 4 | *Salmonella* sp. | 16.9 | 28.9 | 22.9 | 28.7 | 22.5 | 27.3 |
| 5 | Not Detected | Undetermined | 32.0 | Undetermined | 29.9 | Undetermined | 28.7 |
| 6 | *Salmonella* sp. | 20.4 | 29.6 | 21.1 | 29.2 | 26.4 | 28.1 |
| 7 | *Salmonella* sp. | 16.6 | 29.0 | 22.0 | 29.1 | 23.0 | 27.4 |
| 8 | Not Detected | Undetermined | 33.2 | Undetermined | 34.7 | Undetermined | 28.8 |
| 9 | *Salmonella* sp. | 15.0 | 28.3 | 19.1 | 30.1 | 25.6 | 28.1 |
| 10 | *Salmonella* sp. | 16.9 | 27.4 | 18.4 | 30.8 | 22.9 | 27.5 |
| 11 | *Salmonella* sp. | 16.2 | 27.5 | 19.2 | 29.4 | 18.8 | 27.2 |
| 12 | *Salmonella* sp. | 16.1 | 28.4 | 20.2 | 29.3 | 18.5 | 27.3 |
| 13 | *Salmonella* sp. | 14.7 | 29.7 | 18.6 | 29.7 | 19.2 | 27.0 |
| 14 | *Salmonella* sp. | 14.9 | 31.1 | 18.5 | 29.5 | 22.5 | 27.4 |
| 15 | Not Detected | Undetermined | 31.7 | Undetermined | 30.6 | Undetermined | 28.5 |
| 16 | *Salmonella* sp. | 16.0 | 29.5 | 21.3 | 30.2 | 17.8 | 28.3 |
| 17 | Not Detected | Undetermined | 29.2 | Undetermined | 30.1 | Undetermined | 28.6 |
| 18 | Not Detected | Undetermined | 28.0 | Undetermined | 30.1 | Undetermined | 28.5 |
| 19 | Not Detected | Undetermined | 29.3 | Undetermined | 30.3 | Undetermined | 28.4 |
| 20 | Not Detected | Undetermined | 30.1 | Undetermined | 30.1 | Undetermined | 28.5 |
| 21 | *Salmonella* sp. | 14.4 | 31.2 | 17.2 | 32.2 | 18.2 | 27.1 |
| 22 | *Salmonella* sp. | 15.1 | 29.4 | 19.6 | 29.1 | 18.5 | 27.3 |
| 23 | *Salmonella* sp. | 14.9 | 29.3 | 18.1 | 29.9 | 18.3 | 27.7 |
| 24 | *Salmonella* sp. | 16.5 | 29.0 | 23.5 | 32.6 | 22.8 | 27.4 |
| 25 | *Salmonella* sp. | 15.1 | 27.5 | 21.0 | 28.9 | 18.7 | 27.3 |

TABLE 6

Enrichment: 96 hr at ambient

| Sample Name | FDA BAM confirmed | PrepSEQFP | | PrepSEQFA | |
|---|---|---|---|---|---|
| | | FAM (SE) | VIC (IPC) | FAM (SE) | VIC (IPC) |
| 1 | Not Detected | Undetermined | 29.3 | Undetermined | 30.1 |
| 2 | Not Detected | Undetermined | 29.8 | Undetermined | 30.4 |
| 3 | *Salmonella* sp. | 18.5 | 28.2 | 22.3 | 28.8 |
| 4 | Not Detected | Undetermined | 30.7 | Undetermined | 30.0 |
| 5 | Salmonella sp. | 18.2 | 28.7 | 23.6 | 29.0 |
| 6 | Not Detected | Undetermined | 31.4 | Undetermined | 30.9 |
| 7 | *Salmonella* sp. | 20.9 | 29.5 | 25.6 | 29.5 |

TABLE 6-continued

| | | Enrichment: 96 hr at ambient | | | |
|---|---|---|---|---|---|
| Sample | | PrepSEQFP | | PrepSEQFA | |
| Name | FDA BAM confirmed | FAM (SE) | VIC (IPC) | FAM (SE) | VIC (IPC) |
| 8 | *Salmonella* sp. | 19.4 | 27.6 | 25.4 | 29.3 |
| 9 | *Salmonella* sp. | 17.2 | 27.5 | 21.5 | 28.9 |
| 10 | *Salmonella* sp. | 17.3 | 28.2 | 22.8 | 28.9 |
| 11 | *Salmonella* sp. | 17.3 | 28.6 | 21.8 | 28.8 |
| 12 | *Salmonella* sp. | 18.2 | 29.3 | 24.3 | 29.1 |
| 13 | *Salmonella* sp. | 16.4 | 29.8 | 21.1 | 28.9 |
| 14 | Not Detected | Undetermined | 32.2 | Undetermined | 30.4 |
| 15 | *Salmonella* sp. | 19.5 | 29.7 | 23.3 | 29.1 |
| 16 | Not Detected | Undetermined | 31.5 | Undetermined | 30.0 |
| 17 | *Salmonella* sp. | 17.1 | 29.6 | 22.9 | 29.0 |
| 18 | Not Detected | Undetermined | 30.0 | Undetermined | 30.0 |
| 19 | Not Detected | Undetermined | 31.5 | Undetermined | 30.0 |
| 20 | Not Detected | Undetermined | 30.3 | Undetermined | 30.1 |
| 21 | *Salmonella* sp. | 16.1 | 28.2 | 23.5 | 29.0 |
| 22 | *Salmonella* sp. | 16.1 | 27.6 | 24.1 | 29.1 |
| 23 | *Salmonella* sp. | 18.0 | 27.9 | 22.3 | 29.1 |
| 24 | *Salmonella* sp. | 19.0 | 28.5 | 22.0 | 28.9 |
| 25 | *Salmonella* sp. | 18.0 | 27.4 | 22.6 | 29.0 |

TABLE 7

| | | Enrichment: 96 hr at ambient, then 24 hr in TSB + ferrous sulfate (US FDA BAM) | | | |
|---|---|---|---|---|---|
| Sample | FDA BAM | PrepSEQFP | | PrepSEQFA | |
| Name | confirmed | FAM (SE) | VIC (IPC) | FAM (SE) | VIC (IPC) |
| 1 | Not Detected | Undetermined | Undetermined | Undetermined | 30.4 |
| 2 | Not Detected | Undetermined | 30.9 | Undetermined | 30.2 |
| 3 | *Salmonella* sp. | 15.6 | 34.9 | 18.8 | 30.1 |
| 4 | Not Detected | 38.4 | 30.9 | Undetermined | 30.5 |
| 5 | *Salmonella* sp. | 15.0 | 36.4 | 18.2 | 30.3 |
| 6 | Not Detected | Undetermined | 31.7 | Undetermined | 30.4 |
| 7 | *Salmonella* sp. | 15.6 | 34.5 | 19.0 | 30.2 |
| 8 | *Salmonella* sp. | 15.9 | 36.0 | 20.5 | 30.3 |
| 9 | *Salmonella* sp. | 14.9 | 35.6 | 23.5 | 29.1 |
| 10 | *Salmonella* sp. | 15.1 | 35.2 | 25.5 | 29.5 |
| 11 | *Salmonella* sp. | 14.8 | 37.8 | 25.0 | 29.5 |
| 12 | *Salmonella* sp. | 15.1 | 36.1 | 20.4 | 29.7 |
| 13 | *Salmonella* sp. | 14.3 | Undetermined | 19.8 | 30.6 |
| 14 | Not Detected | Undetermined | 31.2 | Undetermined | 30.2 |
| 15 | *Salmonella* sp. | 15.1 | 37.0 | 20.4 | 29.2 |
| 16 | Not Detected | Undetermined | 31.1 | Undetermined | 31.2 |
| 17 | *Salmonella* sp. | 23.5 | 36.7 | 21.8 | 29.0 |
| 18 | Not Detected | Undetermined | 31.4 | Undetermined | 30.6 |
| 19 | Not Detected | Undetermined | 31.8 | Undetermined | 30.5 |
| 20 | Not Detected | Undetermined | 31.1 | Undetermined | 30.6 |
| 21 | *Salmonella* sp. | 15.1 | 36.8 | 20.6 | 29.0 |
| 22 | *Salmonella* sp. | 15.1 | 36.6 | 19.4 | 31.0 |
| 23 | *Salmonella* sp. | 14.8 | 37.3 | 22.1 | 30.8 |
| 24 | *Salmonella* sp. | 15.9 | Undetermined | 22.4 | 31.0 |
| 25 | *Salmonella* sp. | 14.4 | Undetermined | 18.7 | 30.2 |

TABLE 8

| Map Positions for the primers and probes. | | |
|---|---|---|
| accession | assay map position | Assay id |
| AB041905.1 | 7810 ... 7837 ... 7895 | 27320 |
| AB041905.1 | 7804 ... 7823 ... 7886 | 27316 |
| AB041905.1 | 7792 ... 7823 ... 7887 | 27319 |
| AB041905.1 | 7729 ... 7759 ... 7815 | 27318 |
| AB041905.1 | 7698 ... 7741 ... 7783 | 27317 |
| AB041905.1 | 7435 ... 7553 ... 7640 | 27293 |

Example 4

*Salmonella* Serotype *Enteritidis* Detection Assay in Lyophilized Format to Simplify Workflow New formulations and methods were established to create a lyophilized FAST PCR multiplex *S. Enteritidis* detection test. Lyophilization of the test was optimized in two different configurations: bead-format and cake-format. Both formats were made according to the process that consists of the following major steps:

Bulk solution preparation and dispensing of 15 μl per unit.

Figure 3:
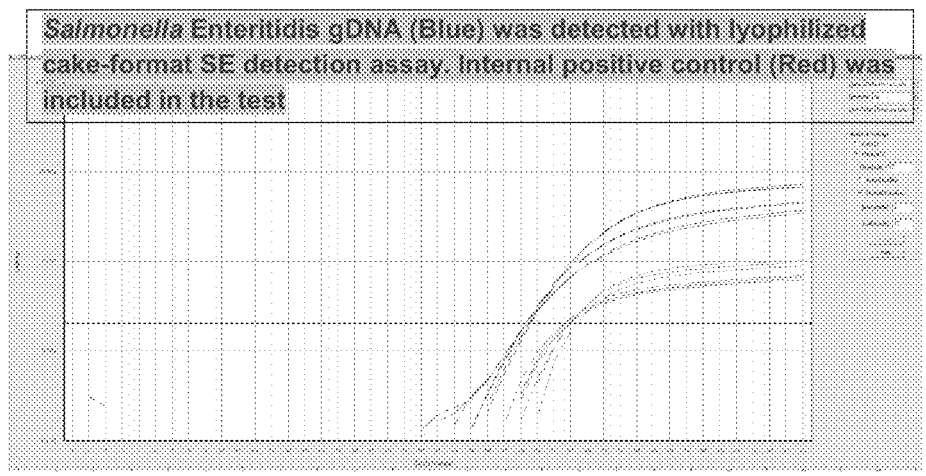
FIG. 3 shows an example method for detecting S. Enteritidis and results using a lyophilized cake format detection assay.

For the cake format an optimized formulation of excipient comprising a mix of Mannitol-Sucrose-PEG was used and all PCR reagents, including Taq polymerase, DNTPs, Buffer components, IPC primers, IPC probe and IPC DNA template. An example assay and results using the lyophilized cake format detection assay is shown in FIG. 3.

Figure 4:
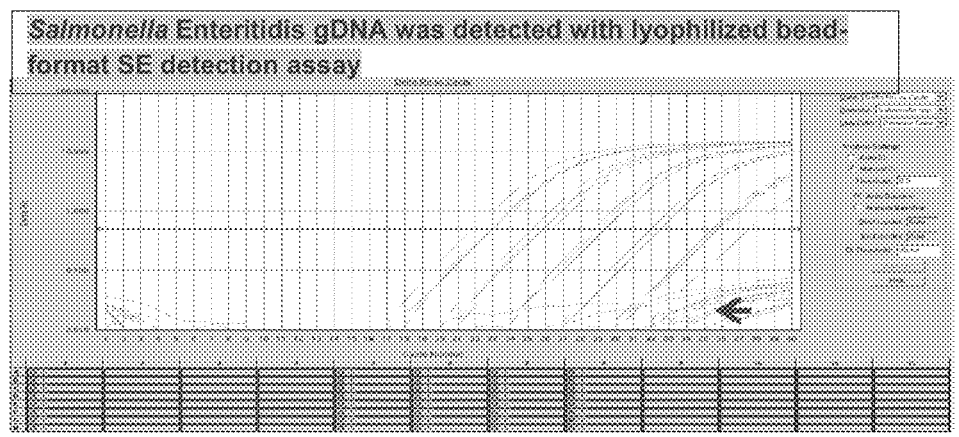
FIG. 4 shows an example method for detecting S. Enteritidis and results using a lyophilized bead-format detection assay.

For the bead-format formulation, the excipient was formulated comprising a mix of Sucrose, Mannitol, and PEG and all PCR reagents; the mix also included Taq polymerase, DNTPs, Buffer components, IPC primers, IPC probe and IPC DNA template. An example assay and results using the bead-format formulation and results obtained therein are shown in FIG. 4.

Lyophilized method formats described herein provides several advantages such as:
 A longer shelf life
 Ambient shipping
 Reduction of storage and transportation costs
 Easy-to-use
 Reduced operator related errors
 Consistent results Lyophilized formats may be used with the kits of the disclosure as described in earlier sections. Furthermore compositions of the disclosure may be lyophilized.

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modification may be made without departing from the essential teachings of the invention.

What is claimed is:

1. A method for determining the presence of S. Enteritidis in a sample comprising:
    combining the sample with a culture medium for enriching Salmonella species for a time sufficient to generate a sample enriched for said species;
    extracting nucleic acid from at least some of the enriched sample to obtain extracted nucleic acid;
    contacting the extracted nucleic acid with at least one primer pair selected from a first primer pair of SEQ ID NO:1 and SEQ ID NO:3, a second primer pair of SEQ ID NO:10 and SEQ ID NO: 12, and a third primer pair of SEQ ID NO: 13 and SEQ ID NO: 15, under real-time polymerase chain reaction (PCR) amplification conditions to generate amplified nucleic acid; and
    detecting at least some of the amplified nucleic acid, thereby determining the presence of S. Enteritidis in the sample, wherein the method does not cross-react with S. Paratyphi C.

2. The method of claim 1 wherein the detecting comprises:
    contacting the amplified nucleic acid with a probe; and
    detecting the hybridization of the probe with the amplified nucleic acid.

3. The method of claim 2, wherein amplification product generated using the first primer pair is detected using a first probe of SEQ ID NO:2, amplification product generated using the second primer pair is detected using a second probe of SEQ ID NO: 11, and amplification product generated using the third primer pair is detected using a third probe of SEQ ID NO: 14.

4. The method of claim 1 comprising:
contacting the extracted nucleic acid with the first primer pair of SEQ ID NO: 1 and SEQ ID NO:3, under real-time PCR amplification conditions to generate amplified nucleic acid; and
detecting at least some of the amplified nucleic acid, thereby determining the presence of *S. Enteritidis* and not *S. Paratyphi* C in the sample, wherein the detecting comprises:
contacting the amplified nucleic acid with a probe of SEQ ID NO:2 or a labeled derivative thereof.

5. The method of claim 1 comprising:
contacting the extracted nucleic acid with the second primer pair of SEQ ID NO: 10 and SEQ ID NO: 12, under real-time PCR amplification conditions to generate amplified nucleic acid; and
detecting at least some of the amplified nucleic acid, thereby determining the presence of *S. Enteritidis* and not *S. Paratyphi* C in the sample, wherein the detecting comprises:
contacting the amplified nucleic acid with a probe of SEQ ID NO: 11 or a labeled derivative thereof.

6. The method of claim 1 comprising:
contacting the extracted nucleic acid with the third primer pair of SEQ ID NO: 13 and SEQ ID NO: 15, under real-time PCR amplification conditions to generate amplified nucleic acid; and
detecting at least some of the amplified nucleic acid, thereby determining the presence of *S. Enteritidis* and not *S. Paratyphi* C in the sample, wherein the detecting comprises:
contacting the extracted nucleic acid with a probe of SEQ ID NO: 14 or a labeled derivative thereof.

7. The method of claim 1 wherein the method comprises:
contacting the extracted nucleic acid with at least two primer pairs, the two primer pairs selected from a first primer pair of SEQ ID NO: 1 and SEQ ID NO:3, a second primer pair of SEQ ID NO: 10 and SEQ ID NO: 12, and a third primer pair of SEQ ID NO: 13 and SEQ ID NO: 15, under real-time PCR amplification conditions to generate amplified nucleic acid; and
detecting at least two sets of amplified nucleic acids, thereby determining the presence of *S. Enteritidis* in the sample.

8. The method of claim 7, wherein the at least two primer pairs comprise:
a first primer pair of SEQ ID NO: 13 and SEQ ID NO: 15, and a second primer pair of SEQ ID NO: 10 and SEQ ID NO: 12.

9. The method of claim 7, wherein the at least two primer pairs comprise:
a first primer pair of SEQ ID NO: 1 and SEQ ID N0:3, and a second primer pair of SEQ ID NO: 13 and SEQ ID NO: 15.

10. The method of claim 7, wherein the at least two primer pairs comprise:
a first primer pair of SEQ ID NO: 1 and SEQ ID NO:3, and a second primer pair of SEQ ID NO: 10 and SEQ ID NO: 12.

11. The method of claim 1, wherein the real-time PCR amplification comprises a 5' nuclease assay.

12. The method of claim 1, wherein the step of detecting at least some of the amplified nucleic acid product comprises fluorescent detection.

* * * * *

SEQUENCE LISTING

```
<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agggcgaggt ttgaaccaa                                                19

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
atgctcagct gctccac                                                  17

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggattcccat agctgtagct ttgtt                                         25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcagtgtaca gggcaaaata gcaata                                        26

<210> SEQ ID NO 5
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cccatctcaa aaatct                                                      16

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtagaaatc gccgtacacg ag                                               22

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agtgtggtga cccccatct                                                   19

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tcgccgtaca cgagctt                                                     17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaacctcgcc ctcacattca                                                  20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttatgaatg tgagggcgag gttt                                             24

<210> SEQ ID NO 11
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
atgctcagct gctccac                                                    17

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aggattccca tagctgtagc tttg                                            24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggtttgaac caagtggagc a                                               21

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aaacaacgcg aaccatg                                                    17

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccactgacag gattcccata gc                                              22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atatcgtcgt tgctgcttcc                                                 20

<210> SEQ ID NO 17
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 17
tcggtcctgc tgtagatgc                                                    19

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cattgttcca ccgtcactttt g                                                21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
atcggtcctg ctgtagatgc                                                   20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ctcatcggtc ctgctgtaga t                                                 21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
aggcgctcat cggtcctgct gt                                                22
```